(12) United States Patent
Arterburn et al.

(10) Patent No.: US 8,715,529 B1
(45) Date of Patent: May 6, 2014

(54) SYNTHESIS AND APPLICATIONS OF TRIAZABOROLOPYRIDINIUM COMPOUNDS AND SUBSTITUTED TRIAZABOROLOPYRIDINIUM COMPOUNDS AND METHODS OF USE

(71) Applicant: Arrowhead Center, Inc., Las Cruces, NM (US)

(72) Inventors: Jeffrey B. Arterburn, Las Cruces, NM (US); Charles B. Shuster, Las Cruces, NM (US); Kevin D. Houston, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 0 days.

(21) Appl. No.: 13/747,674

(22) Filed: Jan. 23, 2013

Related U.S. Application Data

(60) Provisional application No. 61/589,709, filed on Jan. 23, 2012.

(51) Int. Cl.
*C09K 11/06* (2006.01)
*A61K 31/69* (2006.01)

(52) U.S. Cl.
USPC ........................ 252/301.16; 514/64

(58) Field of Classification Search
USPC ........................ 252/301.16; 514/64
See application file for complete search history.

(56) References Cited

U.S. PATENT DOCUMENTS

| | | | |
|---|---|---|---|
| 3,073,819 A | 1/1963 | Straub et al. |
| 3,468,882 A | 9/1969 | Laskowski |
| 3,557,142 A | 1/1971 | Bell |
| 3,630,962 A | 12/1971 | Stapfer et al. |
| 4,332,948 A | 6/1982 | Sakal et al. |
| 5,023,334 A | 6/1991 | Rector et al. |
| 5,187,288 A | 2/1993 | Kang et al. |
| 5,326,692 A | 7/1994 | Brinkley et al. |
| 5,338,854 A | 8/1994 | Kang et al. |
| 5,446,157 A | 8/1995 | Morgan et al. |
| 5,498,641 A | 3/1996 | Urano et al. |
| 5,573,909 A | 11/1996 | Singer et al. |
| 6,001,999 A | 12/1999 | Wolfbeis et al. |
| 6,106,999 A | 8/2000 | Ogiso et al. |
| 6,207,464 B1 | 3/2001 | Karandikar et al. |
| 6,627,759 B1 | 9/2003 | Smith et al. |
| 6,689,494 B1 | 2/2004 | Karandikar |
| 6,805,978 B2 | 10/2004 | Murase et al. |
| 6,828,321 B2 | 12/2004 | Lee et al. |
| 6,903,214 B1 | 6/2005 | Owczarczyk |
| 7,074,503 B2 | 7/2006 | Helber et al. |
| 7,112,680 B2 | 9/2006 | Hofmann et al. |
| 7,220,732 B2 | 5/2007 | O'Shea et al. |
| 7,300,709 B2 | 11/2007 | Owczarczyk et al. |
| 7,329,466 B2 | 2/2008 | Vargas et al. |
| 7,462,404 B2 | 12/2008 | Kathirgamanathan et al. |
| 2005/0215588 A1 | 9/2005 | Nielsen et al. |
| 2006/0084732 A1 | 4/2006 | Shakely et al. |

FOREIGN PATENT DOCUMENTS

| | | | | |
|---|---|---|---|---|
| CN | 101928472 A | * | 12/2010 | ............. C09K 11/06 |
| JP | 60190461 A | | 9/1985 | |
| KR | 2009007075 | | 1/2009 | |

OTHER PUBLICATIONS

"Synthesis and photophysical characterization of novel 2-hydrazinopyridine based fluorophores", Poster, Aug. 2009.
Hapuarachchige, Sudath et al., "Design and Synthesis of a New Class of Membrane-Permeable Triazaborolopyridinium Fluorescent Probes", J. Am. Chem. Soc., vol. 133, American Chemical Society, Apr. 7, 2011, 6780-6790.
Senthilkumar, Sadasivam et al., "Photophysical Properties of Coumarin-30 Dye in Aprotic and Protic Solvents of Varying Polarities", Photochem. Photobiol., vol. 80, American Society for Photobiology, 2004, 104-111.
Wu, L , "Syntheses of Highly Fluorescent GFP-Chromophore Analogues", J. Am. Chem. Soc., vol. 130, American Chemical Society, 2008, 4089-4096.

\* cited by examiner

*Primary Examiner* — Charanjit Aulakh
(74) *Attorney, Agent, or Firm* — Deborah A. Peacock; Isaac Estrada; Peacock Myers, P.C.

(57) ABSTRACT

The present invention is a class of fluorescent compounds derived from hydrazine-2-yl-pyridine containing a triazaborolopyridinium core. The compounds are prepared using a stepwise procedure that begins with a reaction of a hydrazinylpyridine with an aldehyde or ketone to produce a hydrazine. A general formula for the invention is

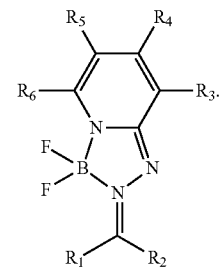

20 Claims, 17 Drawing Sheets

SYNTHESIS AND APPLICATIONS OF TRIAZABOROLOPYRIDINIUM COMPOUNDS AND SUBSTITUTED TRIAZABOROLOPYRIDINIUM COMPOUNDS AND METHODS OF USE

CROSS-REFERENCE TO RELATED APPLICATIONS

This application claims priority to and the benefit of the filing of U.S. Provisional Patent Application Ser. No. 61/589,709, entitled "Synthesis and Applications of Triazaborolopyridinium Compounds and Substituted Triazaborolopyridinium Compounds and Methods of Use", filed on Jan. 23, 2012, and the specification and claims thereof are incorporated herein by reference.

BACKGROUND OF THE INVENTION

1. Field of the Invention (Technical Field)

The present invention relates to dyes, quenching agents and derived conjugates for molecular and cellular imaging.

2. Description of Related Art

Fluorescent dyes, quenching agents, and derived conjugates serve as essential tools for molecular and cellular imaging, flow cytometrey, and a wide variety of applications in biotechnology. Large biomolecules such as DNA, proteins and antibodies are routinely labeled with fluorescent dyes based on fluoroscein, rhodamine, cyanine, or boron dipyrromethene (BODIPY) dyes. Labeling with fluorescent dyes affords a convenient, inexpensive alternative to radiolabeling, and increases the diversity of possible experimental designs for live cell imaging, in vivo pharmacokinetic and metabolism studies. The large size, polycyclic aromatic structures and presence of charged functional groups associated with the majority of fluorescent dyes that are currently in use presents a major challenge when applied to the development of small molecule conjugates, where the physicochemical properties of the dye may dramatically alter the solubility, biodistribution and receptor binding properties of the conjugate. A significant need exists for the development of new biocompatible fluorescent cores that exhibit good aqueous solubility, membrane permeability, lack of toxicity, and favorable photophysical properties, chemical and photostability.

BRIEF SUMMARY OF THE INVENTION

One embodiment of the present invention comprises a fluorescent composition having Formula I, or its enantiomer, diastereomer, stereoisomer, and pharmaceutical salt thereof, Formula I comprising:

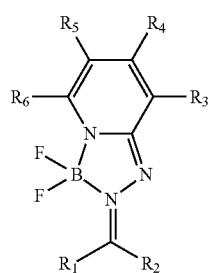

Formula I wherein, $R_1$ and $R_2$ are independently selected from H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound and $R_3$, $R_4$, $R_5$, and $R_6$ are independently selected from H, F, Cl, Br, I, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, thiol, sulfide, sulfoxide, sulfone, sulfonate, sulfoximine, urea, carbamate, maleimide, triazole, tetrazine, isothiocyanate, thiourea linear or branched carbon chain or ring, the carbon chain optionally substituted with F, Cl, Br, I or a $C_1$ to $C_{27}$ carbon substituted compound, acyl, compound, heterocyclic aromatic compound, aromatic compound, enol, enolate, ester enolate, amide. In this embodiment, $R_1$ is not phenyl or 4-(thiophen-2-yl)phenyl, $R_2$ is not phenyl or 4-(thiophen-2-yl)phenyl, and $R_5$ is not Br or 4-phenyl-1H-1,2,3-triazol-1-yl.

In one embodiment of the present invention, $R_5$ of Formula I is attached to a molecule to produce a conjugated entity. The molecule comprises an organic compound, such as but not limited to a carbohydrate, a lipid, triacylglycerol, sterol, fatty acid ester, phospholipid, phosphoglyceride, sphingolipid, ceramide, an amino acid, a peptide, a protein, antibody, a nucleic acid, a steroid, a vitamin, a cofactor, or a biotin. The molecule can also comprise a synthetic compound, such as but not limited to a biologically active compound, an enzyme inhibitor, an agonist, an antagonist, anticancer, antimicrobial, antiviral, antifungal, antiparasitic, antiinflammatory, cardiovascular, antidiabetic, a pharmaceutical, and analogs thereof. The synthetic compound can also be 17-alpha-ethynylestradiol and/or MSTLC.

In another embodiment of the present invention $R_3$ of Formula I is a H, $R_4$ of Formula I is a H, and $R_6$ of Formula I is a H. In a further embodiment of the present invention, $R_1$ and $R_2$ of Formula I together form a cyclopentyl. In this embodiment, $R_5$ of Formula I can be a H, a carboxy-succinimidyl ester, a but-3-yn-1-amine, a but-4-yl-1-amine, a N-(2-(2-(2-tert-butyl-carbamylethoxy)ethoxy)ethyl)carboxamide, a 4-butyl-1-triphenylphosphonium-3-propanamide, a N-(2-(2-(2-(2-azidoethoxy)ethoxy)ethoxy)ethyl)carboxamide, or a 17-ethynyl-estra-1,3,5(10)-triene-3,17-diol, $R_3$ of Formula I is a H, $R_4$ of Formula I is a H, and $R_6$ of Formula I is a H.

In another embodiment of the present invention, $R_1$ of Formula I is a methyl, $R_2$ of Formula I is a methyl and $R_5$ of Formula I is [(2R)-2-amino-3-[[(4-methoxyphenyl)diphenylmethyl]thio]-N-[4-[3-butyn-1-yl]propanamide, $R_3$ of Formula I is a H, $R_4$ of Formula I is a H, and $R_6$ of Formula I is a H.

In yet another embodiment of the present invention, $R_1$ and $R_2$ of Formula I together form a fluorene. In this embodiment, $R_5$ of Formula I can be a carboxy-succinimidyl ester, a hept-6-ynoic-succinimidyl ester, a hydrazide, a prop-2-enoic-tert-butyl ester, a N-(2-(2-(2-aminoethoxy)ethoxy)ethyl)carboxamide, a but-3-yn-1-amine, a but-4-yl-1-amine, a N-(2-(2-(triphenylphosphonium-3-propanamido)ethoxy)ethoxy)ethyl)carboxamide, a but-3-yn-1-triphenylphosphonium-3-propanamide, a 4-butyl-1-triphenylphosphonium-3-propanamide, a N-(2-(2-(2-(2-azidoethoxy)ethoxy)ethoxy)ethyl)hept-6-ynoic-carboxamide, or a N-(2-(2-(2-(2-azidoethoxy)ethoxy)

ethoxy)ethyl)carboxamide, $R_3$ of Formula I is a H, $R_4$ of Formula I is a H, and $R_6$ of Formula I is a H. In an alternative embodiment, the benzene rings of the fluorene are unsubstituted.

One embodiment of the present invention comprises a process for preparing a composition having Formula I. The process comprises reacting a hydrazinylpyridine with an aldehyde or ketone, producing a hydrazine, subjecting the hydrazine to a cyclization reaction by adding a boron trifluoride and an amine base, producing a triazaborolopyridinium core structure, and reacting one or more substituents to produce Formula I.

Another embodiment of the present invention comprises the fluorescent composition of Formula I wherein $R_1$ and $R_2$ together form a substituted fluorene (see below).

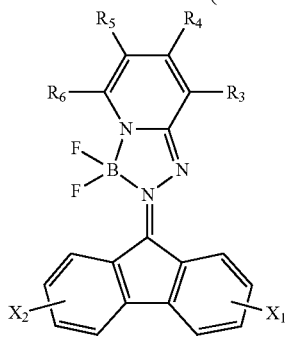

In this embodiment $X_1$ and $X_2$ are independently selected from H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound. In optional embodiments, $X_1$ is a H, $X_2$ is a H, $R_5$ of Formula I is a prop-2-enoic-tert-butyl ester, a N-(2-(2-(2-aminoethoxy)ethoxy)ethyl)carboxamide, a but-3-yn-1-amine, a but-4-yl-1-amine, a N-(2-(2-(2-(triphenylphosphonium-3-propanamido)ethoxy)ethoxy)ethyl)carboxamide, a but-3-yn-1-triphenylphosphonium-3-propanamide, a 4-butyl-1-triphenylphosphonium-3-propanamide, or a carboxysuccinimidyl ester, $R_3$ of Formula I is a H, $R_4$ of Formula I is a H, and $R_6$ of Formula I is a H.

In another embodiment of the present invention, the fluorescent composition of Formula I includes $R_1$ and $R_2$ together forming a heterocycloalkenyl (see below).

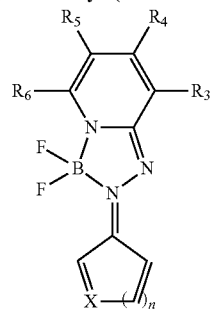

In this embodiment, X is O, S, NH or $R_9$, wherein $R_9$ is selected from $CH_2$, H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound, and n is 1, 3, or 5.

In another embodiment of the present invention, the fluorescent composition of Formula I includes $R_1$ and $R_2$ together forming a heterocycloalkyl (see below).

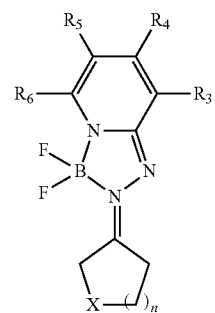

In this embodiment, X is from $CH_2$, O, S, NH, or $NR_9$, wherein $R_9$ is selected from H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound, and n is 1, 3, or 5.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

LIST OF ABBREVIATIONS

Figure 1:
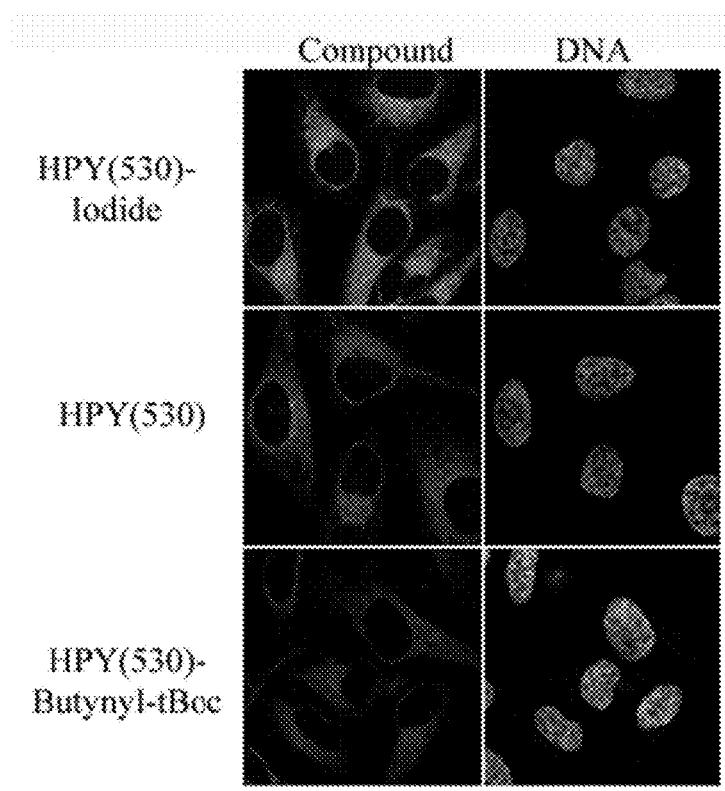
FIG. 1 illustrates HeLa cells treated with HPY(530) compounds to show the HPY(530) staining capability.

| | |
|---|---|
| µg | microgram |
| µM | micromolar |
| Ag(OTf) | Silver triflate |
| Boc | ᵗButoxycarbonyl |
| BODIPY | 4,4-difluoro-4-bora-3a,4a-diaza-s-indacene |
| BSS | Earle's Balanced Salt Solution |
| CH₃CN | Acetonitrile |
| DBU | 1,8-Diazabicyclo[5.4.0]undec-7-ene |
| DEA | Diethylamine |
| DIC | Differential Interference Contrast |
| DMF | N,N-Dimethylformamide |
| DMSO | Dimethylsulfoxide |
| DNA | Deoxyribonucleic acid |
| EE | 17-α-ethynylestradiol |
| ER | Estrogen receptor |
| ESI | Electron Spray Ionization |
| EtOAc | Ethyl acetate |
| EtOH | Ethanol |
| FBS | Fetal Bovine Serum |
| FT-IR | Fourier Transform Infrared |
| GPR30 | G Protein Coupled Receptor 30 |
| HeLa cells | Cultured cancerous tumor cells of Henrietta Lacks |
| HPLC | High Performance Liquid Chromatography |
| HPLC-MS | High Performance Liquid Chromatography with Mass Spectrometer |
| HPY | 2-Hydrazinylpyridine based |
| HRMS | High Resolution Mass Spectrometer |
| IC | Intersystem Crossing |
| MeOH | Methanol |
| mg | milligram |
| MHz | Megahertz |
| mM | millimolar |
| mmol | millimoles |
| mol | moles |
| MSTLC | Methoxy-S-trityl-L-cysteine |
| N.R. | No reaction |
| NADPH | Nicotinamide Adenine Dinucleotide Phosphate |
| NaH | Sodium hydride |
| NBD | Nitro benxozadiazole |
| NCA | N-carboxyanhydride |
| NHS | N-Hydroxysuccinimide |
| NIR | Near Infrared |
| NMP | N-Methyl-2-Pyrrolidine |
| NMR | Nuclear Magnetic Resonance |
| PBS | Phosphate Buffered Saline |
| PET | Positron Emission Tomography |
| Ph(OAc)₂ | Palladium acetate |
| pH$_e$ | Extracellular pH |
| pKa$_e$ | Excited state pKa |
| PMT | Photomultiplier tube |
| POPOP | 5-Phenyl-2-[4-(5-phenyl-1,3-oxazol-2-yl)phenyl]-1,3-oxazole |
| psi | pounds per square inches |
| SPECT | Single Photon Emission Computed Tomography |
| STLC | S-Trityl-L-cysteine |
| TBP | Triazaborolopyridinium |
| TFA | Trifluoroacetic acid |
| THF | Tetrahydrofuran |
| TMS | Trimethylsilyl |
| TPB | 4-(thiophen-2-yl)benzaldehyde |
| ε | Molar extinction coefficient |
| λ$_{emi}$ | Emission maximum |
| λ$_{max}$ | Absorption maximum |
| Φ | Quantum yield |

DETAILED DESCRIPTION OF THE INVENTION

"Carbon chain or ring" is defined throughout the specification and claims as including but not limited to $C_1$-$C_{27}$ alkane, $C_1$-$C_{27}$ cycloalkane, $C_1$-$C_{27}$ alkyl, $C_1$-$C_{27}$ cycloalkyl, $C_1$-$C_{27}$ aryl, $C_1$-$C_{27}$ heteroaryl, $C_1$-$C_{27}$ alkene, $C_1$-$C_{27}$ alkyne, $C_1$-$C_{27}$ alkenyl, $C_1$-$C_{27}$ cyloalkenyl, $C_1$-$C_{27}$ aralkyl chain, $C_1$-$C_{27}$ arene, or conjugated $C_1$-$C_{27}$ alkene, combinations thereof or the like.

"Carbon substituted compound" is defined throughout the specification and claims as a compound where one or more hydrogen atoms of a core structure have been replaced with a substituent or functional group. The substituent or functional group is, for example, a linear or branched alkane, cycloalkane, alkyl, cycloalkyl, aryl, heteroaryl, alkene, alkyne, alkenyl, cyloalkenyl, aralkyl chain, arene, conjugated alkene, I, Br, F, Cl, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, thiol, sulfide, sulfoxide, sulfone, sulfonate, sulfoximine, urea, carbamate, maleimide, triazole, tetrazine, isothiocyanate, thiourea.

Embodiments of the present invention preferably comprise a class of fluorescent compounds derived from hydrazine-2-yl-pyridine (referred to herein as HPY dyes) containing a triazaborolopyridinium core. The compounds are prepared using a stepwise procedure that begins with a reaction of a hydrazinylpyridine with an aldehyde or ketone to produce a hydrazone. The pyridin-2-yl hydrazone derivatives are then subjected to a cyclization reaction, which preferably involves a boron trifluoride and amine base, to produce the triazaborolopyridinium core structure. These compounds are intensely colored and exhibit strong absorption and fluorescent emission spectra that are suitable for a wide variety of potential applications. The photophysical and physicochemical properties of the HPY dyes are preferably tunable for a range of excitation and emission properties that depend on the identity of substituents on the pyridyl group, the hydrazone derived from precursor aldehyde or ketones, and the identity of groups attached to the boron atom.

In one embodiment of the present invention, the HPY dyes are suitable as dyes and stains for a variety of specific applications using optical methods for detection, quantification, color and visual appearance. The HPY dyes can be used directly or can be attached to, or incorporated within other compounds, polymers, nanoparticles, films and other materials or media for specific applications and processes. Representative applications of the HPY dyes include, but are not limited to, microscopy, live cell imaging, in vivo imaging, flow cytometry, biomaterial sequencing, biomaterial detection and quantification, biomolecular screening, ligand binding assays, detection of biomarkers, histology, photodynamic processes, and product formulation.

There are many applications for fluorescent dyes that are easily attached to other materials or compounds such as biochemicals and small organic ligands and that result in minimal perturbation of the resulting physicochemical, structural, and biological properties such as binding to biological receptors for targeted imaging and detection applications. These applications include, but are not limited to, the synthesis of optical probes derived from drugs, natural products, and other small molecules identified through chemical biology approaches. There are multiple opportunities for the development of high affinity low molecular weight optical probes and materials incorporating novel fluorescent dyes.

In an embodiment of the present invention, the HPY dyes with a triazaborolopyridinium core are intensely colored and exhibit strong absorption and fluorescent emission spectra that are tunable for a range of excitation and emission for specific applications. The dyes are preferably small, neutral, membrane permeable, and can be incorporated into optical probes and imaging agents using a variety of efficient synthetic approaches such as but not limited to hydrazone formation, catalytic carbon-carbon and carbon-nitrogen coupling on the pyridine ring as exemplified by the Sonogashira coupling of alkyne, Suzuki coupling of boronic acids, 1,3-dipolar "click" cyclization of alkyne and azide groups, and amine coupling to activated nicotinic acid derivatives. The HPY-dyes are preferably compatible with the development of materials and optical probes for live cell and in vivo imaging applications, and the development of other tissue staining, biomolecular screening, assays and optical methods for quantification that do not require fixation and/or permeabilization of cells to permit entry of the dye or optical probe.

One embodiment of the present invention comprises a series of HPY dyes. These dyes were evaluated for cell membrane permeability and imaging properties in HeLa cells using conventional epifluorescence microscopy which revealed rapid uptake throughout the endomembrane network. Details and characterization data are provided in the examples.

The UV-traceable bis-aryl hydrazone chromophore provides a basis for quantitative determination of protein labeling, but the moiety itself is not fluorescent. One embodiment of the present invention uses cyclization chemistry to produce a corresponding triazaborolopyridinium derivative that enables more sensitive detection and quantification of the UV-traceable bis-aryl hydrozone chromophore by fluorescence spectroscopy.

General Structures: HPY

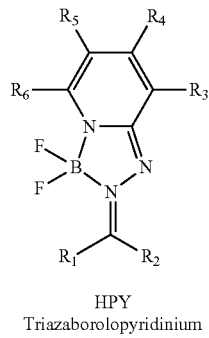

HPY
Triazaborolopyridinium

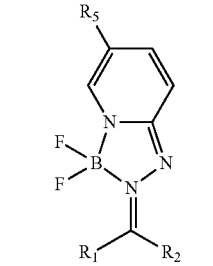

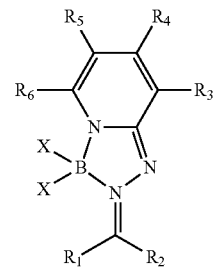

X = O-alkyl, O-aryl
C-alkyl, C-aryl
C-alkenyl, C-alkynyl
N-alkyl, N-aryl

In one embodiment of the present invention, the 3,3-difluoro-2,3-dihydro[1,2,4,3]triazaborolo[4,5-a]pyridin-2-ium-3-uide structure is fluorescent, and has many useful properties and applications as either a singular component, or when attached to other molecular structures. The structure comprises a triazaborolopyridinium chemical structure, fluorescent properties, and has a demonstrated application as fluorescent probes for live cell imaging. The general structure I is representative of difluoro-HPY compounds, and observed the importance that the identity of specific groups or substituents ($R_1$-$R_6$) has on the observed photophysical properties. Each of these positions also represents a site at which other molecular entities can be attached, using a variety of different chemical linkages, which is another important feature of the HPY compounds.

The position and chemical nature of HPY-substituents affects the photophysical properties and provides a method for attachment of HPY dyes to other molecular entities.

The general structure II is representative of difluoro-HPY derivatives with substituents attached to position $R_5$. General structure III is representative of other HPY compounds with substitutions of the fluorine groups by oxygen groups, and with other carbon or nitrogen groups. These substitutions on boron can also be used to modify photophysical properties and can be used as linkages to other molecular structures.

Other Example General Structures for HPY Dyes:
HPY-Fluorenone Cores (see below): These are effective dyes. The substituents ($R_3$-$R_6$) can be varied to adjust the photophysical and physicochemical properties, can be used for connecting linkages to other molecular entities, and can be reactive functional groups that can be used to attach the dyes to other molecular entities. Examples of substituents can be a linear or branched alkane, cycloalkane, alkyl, cycloalkyl, aryl, heteroaryl, alkene, alkyne, alkenyl, cyloalkenyl, aralkyl chain, arene, conjugated alkene, I, Br, F, Cl, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, thiol, sulfide, sulfoxide, sulfone, sulfonate, sulfoximine, urea, carbamate, maleimide, triazole, tetrazine, isothiocyanate, thiourea. Substitutents (X1-X2, etc.) can also be varied to adjust the photophysical and physicochemical properties, on the fluorene ring portion of this core. Examples of substituents for X1 and X2 can be H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound.

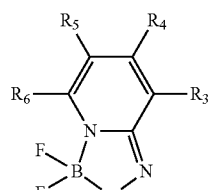

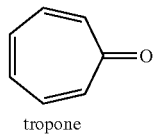

tropone

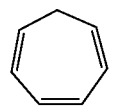

(1Z,3Z,5Z)-cyclohepta-1,3,5-triene

HPY-Cyclopentyl dyes (see below) are effective dyes. They are small and have good water solubility and are excited with 405 nm light (a useful frequency for many instruments). The extension to other ring sizes in the HPY-Cycloalkyl and HPY-Heterocycloalkyl compounds (see below) can also be composed.

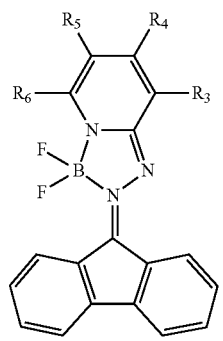

HPY-Fluorene Core

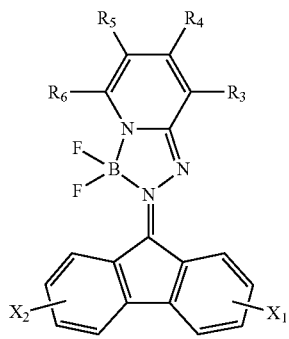

HPY-Fluorene Substituted

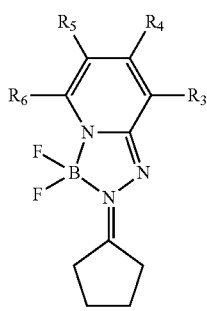

HPY-Cyclopentyl Core

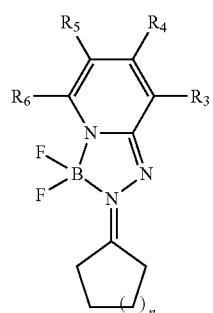

HPY-Cycloalkyl Core
n = 0, 1-12

HPY-Cycloalkenyl and HPY-Heterocycloalkenyl compounds (see below) are related to a specific fluorene class by being "cyclic and conjugated".

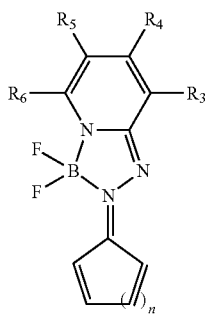

HPY-Cycloalkenyl Core
n = 1, 3, 5

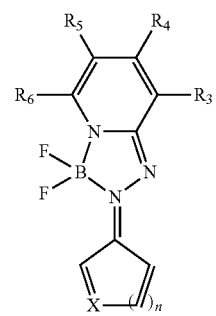

HPY-Heterocycloalkenyl Core
n = 1, 3, 5
X = O, S, NH, $NR_9$

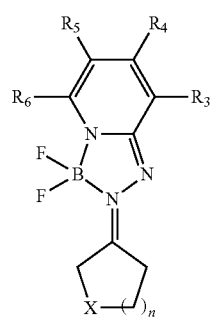

HPY-Heterocycloalkyl Core
n = 0, 1-12
X = O, S, NH, $NR_9$

An example of the HPY-Cycloalkenyl is the tropone derivative shown below:

An example of a HPY-Heterocycloalkyl core is the pyran-compound shown below:

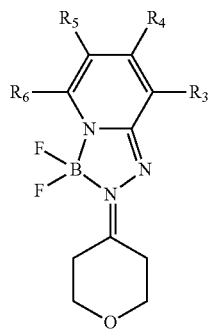

HPY-Carboxylic Acid dyes in the $R_5$ position are effective dyes. The carboxylic acid is a useful functional group for connecting other molecules, and activated esters such as, but not limited to, the N-hydroxysuccinimidyl esters (NHS) react with amines to form carboxamide (amide) bonds. This position can also be used to attach alkyl-azide groups for Click-it labeling. In one example, a hydrazide group is in the $R_5$ position. HPY-Carbonyl cores with other types of carbonyl groups (ketone or aldehyde) are also useful, and the carboxyl/carbonyl groups can be attached at other substitution positions, for example, the $R_3$, $R_4$ or $R_6$ position.

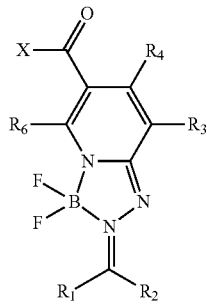

HPY-Carboxyl/Carbonyl Core

The HPY-Propenoxy/Propenone (see below) is related to the above discussion of the carboxyl/carbonyl functional group, with all of the same applications, such as being a useful functional group for connecting other molecules and activated esters, and also for reactions and/or linkages at the conjugated site. An example of the HPY-Propenoxy/Propenone is one in which the X is tert-butyl ester.

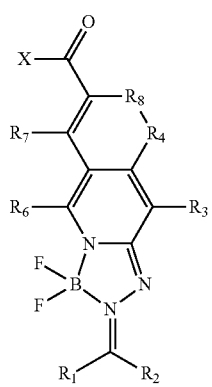

HPY-Propenoxy/Propenone Core

The HPY-Alkynyl and HPY-Alkenyl cores (see below) can be used to attach groups. The HPY-Alkyl is another useful connection. These groups are shown in the $R_5$ position as an example only, but can be placed at the other positions, for example, $R_3$, $R_4$, and $R_6$.

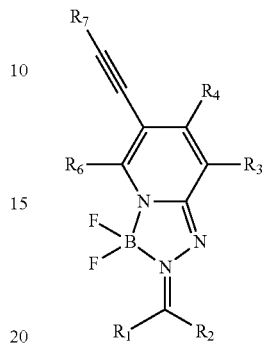

HPY-Alkynyl Core

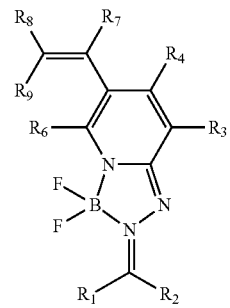

HPY-Alkynyl Core

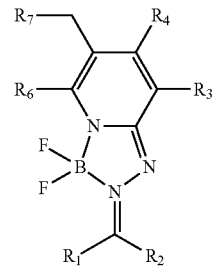

HPY-Alkynyl Core

Below are examples of particular compounds having general structure I, II or III. Each compound is labeled with a number, for example, 1.1 or 2.4. These numbers will be used throughout the specification to refer to the corresponding compound.

Compound Name: HPY(530)
Structure I: $R_1$-$R_2$=fluorene, $R_3$:$R_6$=H

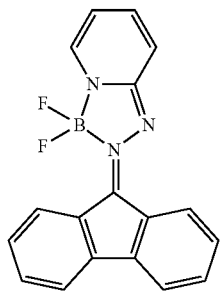

HPY(530)
Chemical Formula: $C_{18}H_{12}BF_2N_3$
Molecular Weight: 319.12
1.0

The HPY(530) structure comprising a fluorene group has an absorption maximum at 530 nm and is a highly fluorescent. The compound is neutral, and is permeable to cell membranes. The extended conjugation of the fluorene group causes a "red-shift" in the absorbance to longer wavelength relative to less conjugated groups. This compound can be used as a dye compound, or as a component of substituted variations with corresponding physicochemical, photophysical, and biological properties that may be advantageous for specific applications.

The HPY(530) is a relatively small fluorophore, neutral, membrane permeable, soluble in a variety of polar and nonpolar solvents, with particularly bright emission properties in octanol (a solvent that mimics the environment of cellular membranes) and a large Stokes shift that provides separation between the absorption and emission spectra. The structure of HPY(530) is substantially planar, and exhibits fluorescence polarization. As a fluorescent scaffold or component of more complicated fluorescent dyes, substituted derivatives are possible on the pyridine ring system and/or the fluorene groups present.

Example: HPY(530) Chemical synthesis, characterization data, photophysical properties.

To a mixture of the hydrazone: (Z)-2-((9H-fluoren-9-ylidene)hydrazono)-1,2-dihydropyridine (0.271, 1 mmol) and $BF_3$-$Et_2O$ (0.705 g, 5 mmol) in dry toluene (5 mL) was added 1,8-diazabicyclo[5.4.0]undec-7-ene (DBU) (0.33 g, 2.2 mmol) and heated at about 90° C. for about 6 hours. Volatiles were removed in vacuo and the residue was dissolved in $CH_2Cl_2$ (25 mL), washed with water, the organic layer was separated, dried over $Na_2SO_4$, and concentrated under reduced pressure. The residue was purified by silica gel column chromatography using $CH_2Cl_2$ eluent, to isolate the product HPY(530) (0.27 g, 84%) as red solid $^1H$ NMR (300 MHz, $CDCl_3$) δ 9.02 (d, J=7.63 Hz, 1H), 8.41 (d, J=7.78 Hz, 1H), 7.61-7.55 (m, 3H), 7.51-7.24 (m, 5H), 6.89 (d, J=8.95 Hz, 1H), 6.47-6.43 (m, 1H); $^{13}C$ NMR (75 MHz, DMSO-$D_6$) δ 141.76, 141.64, 136.0, 132.4, 132.0, 131.3, 128.8, 128.6, 126.5 (t, J=9.98 Hz, 1C), 120.2, 119.9, 113.8, 111.2; $^{19}F$ NMR (300 MHz, DMSO-$D_6$)-151.1 (m, 2F). UV-Vis (EtOH) λhd max: 518 nm; $\epsilon$=31950 M-1 cm-1; $\lambda_{em}$: 535 nm; $\phi_f$=0.66. UV-Vis (octanol) $\lambda_{max}$: 524 nm; $\epsilon$=23870 $M^{-1}$ $cm^{-1}$; $\lambda_{em}$: 557 nm; $\phi_f$=0.80. Log $P_{o/w}$=1.59. HRMS/ESI-TOF (m/z): calcd for $[M+H]^+$ $C_{18}H_{13}BF_2N_3$: 320.1171. found: 320.1165.

Referring to FIG. 1, HPY(530) compounds readily penetrate live HeLa cells. HeLa cells were treated with about 0.5 μM HPY(530)-Iodide, about 0.5 μM HPY(530), or about 10 μM HPY(530)-Butynyl-tBoc for about 30 minutes and imaged live using a 63× objective on a Leica TCS-SP5 II inverted, confocal microscope with resonance scanner.

HPY(530) targeting was conducted in HeLa cells by the following procedure. HeLa cells were seeded in 35 mm glass-bottom FluoroDishes at a density of about 3.0×10$^5$ cells per dish and incubated overnight at about 37° C. and about 5% $CO_2$. Cells were then treated with about 0.5 μM HPY(530), about 0.5 μM HPY(530)-Iodide, or about 10.0 μM HPY(530)-Butynyl-tBoc. The compounds were diluted to a stock solution of 10 mM using DMSO then diluted further to working concentration using minimum essential medium eagle (EMEM). Compounds in EMEM solution were warmed to about 37° C. before treatments. Media from dishes was removed and replaced with working concentration of compound and allowed to incubate at about 37° C. and about 5% $CO_2$ for about 30 minutes.

FIG. 1 illustrates HeLa cells treated with HPY(530) compounds to evaluate their cell staining capacity (left panels). Although all three compounds readily entered the cell within about 30 minutes, HPY(530)-Iodide gave the most intense signal. No specific subcellular localization was observed. No fluorescence from each HPY compound was observed within the nucleus, using Hoechst 3342 stain for DNA to visualize the nucleus (right panels).

Compound Name: HPY(405)

Structure: I: $R_1$-$R_2$=cyclopentyl, $R_3$:$R_6$=H

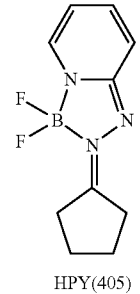

HPY(405)
Chemical Formula: $C_{10}H_{12}BF_2N_3$
Molecular Weight: 223.03
1.1

The HPY(405) structure comprising a cyclopentene group at the $R_1$-$R_2$ position has an absorption maximum at 405 nm and is highly fluorescent. The compound is neutral, and is permeable to cell membranes. The absence of conjugation in the cyclopentene group causes a "blue-shift" in the absorbance to shorter wavelengths relative to more highly conjugated groups. This compound can be used as a dye compound, or as a component of substituted variations with corresponding physicochemical, photophysical, and biological properties that may be advantageous for specific applications.

The HPY(405) is a small fluorophore, neutral, membrane permeable, soluble in water and a variety of other polar and nonpolar solvents, with particularly bright emission properties in octanol (a solvent that mimics the environment of cellular membranes) and a large Stokes shift that provides separation between the absorption and emission spectra. The cyclopentene group contributes greater chemical and photochemical stability to the HPY(405) compounds in comparison to acyclic analogs derived from acetone. The structure of HPY(405) is substantially planar, and exhibits fluorescence polarization. As a fluorescent scaffold or component of more complicated fluorescent dyes, substituted derivatives are possible on the pyridine ring system and/or the cyclopentane groups present.

Example: HPY(405) Chemical synthesis, characterization data, photophysical properties.

To a mixture of hydrazone: (Z)-2-(cyclopentylidenehydrazono)-1,2-dihydropyridine (0.175, 1 mmol) and $BF_3$-$Et_2O$ (0.705 g, 5 mmol) in dry toluene (5 mL) was added DBU (0.33 g, 2.2 mmol) and heated at about 90° C. for about 5 hours. Volatiles were removed in vacuo, the residue was dissolved in $CH_2Cl_2$ (25 mL), washed with water, the organic layer was separated, dried over $Na_2SO_4$ and concentrated under reduced pressure. The residue was purified by silica gel column chromatography using $CH_2Cl_2$ eluent to isolate the product HPY(405) (0.124 g, 56%) as a yellow solid. $^1H$ NMR (300 MHz, $CDCl_3$) δ 7.34 (d, J=6.05 Hz, 1H), 7.29-7.23 (m, 1H), 6.58 (d, J=9.81 Hz, 1H), 6.19-6.15 (m, 1H), 2.92-2.80 (m, 4H), 1.97-1.87 (m, 4H); $^{13}C$ NMR (75 MHz, $CDCl_3$) 172.5, 161.0, 139.9, 134.9, 111.7, 107.8, 32.4, 30.8, 25.3, 24.0; $^{19}F$ NMR (300 MHz, $CDCl_3$)-154.9 (m, 2F). UV-Vis (octanol) $\lambda_{max}$: 396 nm; $\epsilon$=6850 $M^{-1}$ $cm^{-1}$; $\lambda_{em}$: 443 nm and 473 nm; $\phi_f$=0.50.

Compound Name: HPY(530)-Iodide
Structure I: $R_1$-$R_2$=fluorene, $R_3$, $R_4$, $R_6$=H, $R_5$=I

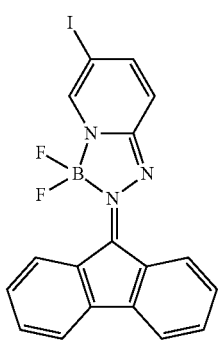

HPY(530)-Iodide
Chemical Formula: $C_{18}H_{11}BF_2IN_3$
Molecular Weight: 445.01
1.2

The HPY(530)-Iodide exhibits favorable photochemical properties that are directly comparable to the simple HPY (530) structure, and is representative of other mono- or polyhalogenated derivatives (halogens=F, Cl, Br, I), so $R_5$ can be F, Cl, Br or I.

The iodide is useful as a reactive group for attaching the fluorescent dye to other molecular structures, notably using metal-mediated coupling reactions, which enables synthesis of a wide variety of fluorescent conjugates.

Example: HPY(530)-Iodide Chemical synthesis, characterization data, photophysical properties.

To a mixture of hydrazone: (Z)-2-((9H-fluoren-9-ylidene)hydrazono)-5-iodo-1,2-dihydropyridine (0.397, 1 mmol) and $BF_3$-$Et_2O$ (0.705 g, 5 mmol) in dry toluene (5 mL) was added DBU (0.33 g, 2.2 mmol) and heated at about 90° C. for about 8 hours. Volatiles were removed in vacuo. The residue was dissolved in dichloromethane (25 mL), washed with water, the organic layer was separated, dried over $Na_2SO_4$ and concentrated under reduced pressure. The residue was purified by silica gel column chromatography using hexanes/EtOAc (70:30) eluent to isolate the product HPY(530)-Iodide (0.426 g, 96%) as a red solid. $^1$H NMR (300 MHz, $CDCl_3$): δ 9.98 (d, J=7.78 Hz, 1H), 8.37 (d, J=7.78 Hz, 1H), 7.79 (s, 1H), 7.60 (dd, J=9.24, 1.91 Hz, 1H), 7.61-7.56 (m, 2H), 7.44 (dt, J=7.48, 7.48, 1.17 Hz, 1H), 7.38 (dt, J=7.48, 7.48, 1.03 Hz, 1H), 7.32 (dt, J=7.63, 7.63, 1.32 Hz, 1H), 7.28 (dt, J=5.72, 5.72, 1.17 Hz, 1H), 6.73 (d, J=9.39 Hz, 1H); $^{13}$C NMR (75 MHz, $CDCl_3$) 159.2, 156.3, 150.7, 148.4, 141.84, 141.71, 141.09, 132.6, 132.1, 131.6, 131.1, 128.6, 128.5, 126.6 (t, J=8.98 Hz, 1C), 120.1, 119.7, 115.2, 70.2; $^{19}$F NMR (300 MHz, $CDCl_3$); δ -149.09 (q, J=28 Hz, 2F). UV-Vis (octanol) $\lambda_{max}$: 537 nm, $\varepsilon$=38250 $M^{-1}$ $cm^{-1}$; $\lambda_{em}$: 560 nm; $\phi_f$: 0.87. Log $P_{o/w}$=0.79. HRMS/ESI-TOF (m/z): calcd for $[M+H]^+$ $C_{18}H_{12}BF_2IN_3$: 446.0167. found: 446.0126.

Referring to FIG. 1, HPY(530)-Iodide shows the most intense signal of the HPY(530)s illustrated in FIG. 1.

Compound Name: HPY(405c)-Iodide
Structure I: $R_1$-$R_2$=cyclopentyl, $R_3$, $R_4$, $R_6$=H, $R_5$=I

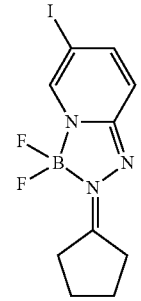

HPY(405)-Iodide
Chemical Formula: $C_{10}H_{11}BF_2IN_3$
Molecular Weight: 348.93
1.3

The HPY(405c)-Iodide exhibits favorable photochemical properties that are directly comparable to the simple HPY (405c) structure, and is representative of other mono- or polyhalogenated derivatives ($R_5$ can comprise halogens=F, Cl, Br, I).

The iodide is useful as a reactive group for attaching the fluorescent dye to other molecular structures, notably using metal-mediated coupling reactions, which enables synthesis of a wide variety of fluorescent conjugates.

Example: HPY(405c)-Iodide Chemical synthesis, characterization data, photophysical properties.

To a mixture of hydrazone: (Z)-2-(cyclopentylidenehydrazono)-5-iodo-1,2-dihydropyridine (0.301 g, 1 mmol) and $BF_3$-$Et_2O$ (0.705 g, 5 mmol) in dry toluene (5 mL) was added DBU (0.33 g, 2.2 mmol) and heated at about 90° C. for about 5 hours. Volatiles were removed in vacuo. The residue was dissolved in $CH_2Cl_2$ (25 mL), washed with water, the organic layer was separated, dried over $Na_2SO_4$ and concentrated under reduced pressure. The residue was purified by silica gel column chromatography using $CH_2Cl_2$ to isolate the product HPY(405)-Iodide (0.273 g, 78%) as a yellow solid. $^1$H NMR (300 MHz, $CDCl_3$) δ 7.53 (bs, 1H), 7.34 (dd, J=9.54, 1.91 Hz, 1H), 6.40 (d, J=9.54 Hz, 1H), 2.91-2.75 (m, 4H), 1.97-1.88 (m, 4H); $^{13}$C NMR (75 MHz, $CDCl_3$) 174.8, 159.2, 146.9, 140.4, 113.9, 66.5, 32.7, 31.0, 25.4, 24.0; $^{19}$F NMR (300 MHz, $CDCl_3$): -154.05 (q, J=30 Hz, 2F). UV-Vis (octanol) $\lambda_{max}$: 411 nm; $\varepsilon$=9500 $M^{-1}$ $cm^{-1}$; $\lambda_{em}$: 461 nm and 495 nm; $\phi_f$=0.32. Log $P_{o/w}$=0.67. HRMS/ESI-TOF (m/z): calcd for $[M+H]^+$ $C_{10}H_{12}BF_2IN_3$: 350.0137. found: 350.0134.

Compound Name: HPY(490)-Carboxylic Acid
Structure I: $R_1$-$R_2$=fluorene, $R_3$, $R_4$, $R_6$=H, $R_5$=carboxy

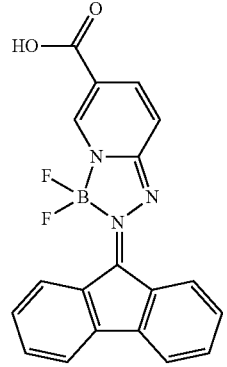

HPY(490)-Carboxylic Acid
Chemical Formula: $C_{19}H_{12}BF_2N_3O_2$
Molecular Weight: 363.13
1.4

The HPY(490)-Carboxylic Acid exhibits favorable photochemical properties with an absorption maximum at 490 nm. The direct comparison of this compound with the simple HPY(530) structure illustrates the important effect that the carboxylic acid group in the $R_5$-position of the pyridinium ring has on the photophysical properties, resulting in a "blueshift" relative to the unsubstituted compound. This compound is representative of other mono- or poly-carboxylated derivatives.

The carboxylic acid group is weakly acidic and ionized under basic conditions, thereby effecting solubility and physicochemical properties, providing greater water solubility, as well as affecting the photophysical properties as described. The carboxylic acid is very useful as a reactive group for attaching the fluorescent dye to other molecular structures, accomplished by activating this group with carboxyl-reactive reagents or through conversion into other activated ester functional groups, accompanied by reactions with amines to synthesize a wide variety of fluorescent conjugates.

Example: HPY(490)-Carboxylic Acid Chemical synthesis, characterization data, photophysical properties.

To a mixture of hydrazone: (Z)-6-((9H-fluoren-9-ylidene)hydrazono)-1,6-dihydropyridine-3-carboxylic acid (0.319 g, 1 mmol) and $BF_3$-$Et_2O$ (0.705 g, 5 mmol) in dry toluene (5 mL) was added DBU (0.33 g, 2.2 mmol) and heated at about 90° C. for about 5 hours. Volatiles were removed in vacuo. The residue was mixed with $CH_2Cl_2$ (25 mL) and water (25 mL) and sonicated for 20 min to facilitate mixing. The red solid was filtered and dried in vacuo to isolate the product HPY(490)-Carboxylic Acid (0.26 g, 72%). $^1$H NMR (300 MHz, DMSO-$D_6$) δ 13.21 (s, 1H), 8.94 (d, J=7.78 Hz, 1H), 8.38 (d, J=1.17 Hz, 1H), 8.26 (d, J=7.63 Hz, 1H), 8.06-8.02 (dd, J=9.24, 1.76 Hz, 1H), 7.88 (dd, J=7.48, 3.81 Hz, 2H), 7.61-7.50 (m, 2H), 7.45-7.36 (m, 2H), 7.12 (d, J=9.39 Hz, 1H); $^{13}$C NMR (75 MHz, DMSO-$D_6$) δ 165.2, 160.9, 151.1, 142.1, 141.9, 141.8, 140.0, 134.2, 133.1, 132.4, 131.5, 130.4, 129.5, 129.1, 126.4 (t, J=9.54 Hz), 121.6, 121.2, 116.1, 113.3; $^{19}$F NMR (300 MHz, DMSO-$D_6$) 6-148.3 (m, 2F); UV-Vis (DMSO) $\lambda_{max}$: 523 nm; $\epsilon$=33350 $M^{-1}$ $cm^{-1}$; $\lambda_{em}$: 571 nm; $\phi_f$=0.07. HRMS/ESI-TOF (m/z): calcd for $[M+H]^+$ $C_{19}H_{13}BF_2N_3O_2$: 364.1141. found: 364.1062.

Compound Name: HPY(490)-NHS Ester
Structure I: $R_1$-$R_2$=fluorene, $R_3$, $R_4$, $R_6$=H, $R_5$=carboxysuccinimidyl ester

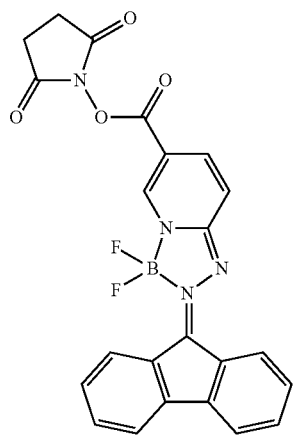

HPY(490)-Carboxylic Acid NHS Ester
Chemical Formula: $C_{23}H_{15}BF_2N_4O_4$
Molecular Weight: 460.20
1.5

The HPY(490)-NHS Ester is an amine-reactive activated ester derivative that is effective for coupling with organic amines to form carboxamide linkages as a method of labeling with this fluorescent dye.

The HPY(490)-NHS Ester is an effective labeling agent for organic amines, and other amine-containing biomolecules such as proteins and antibodies. As a reagent this compound exhibits good chemical stability and easily stored for extended periods with exclusion of water.

Example: HPY(490)-NHS Ester Chemical synthesis, characterization data.

To a mixture of HPY(490)-Carboxylic Acid (0.363 g, 1 mmol) and N-hydroxysuccinimide (0.120 g, 1.05 mmol) in $CH_2Cl_2$ (30 mL) was added N,N'-dicyclohexylcarbodiimide (DCC) (0.216 g, 1.05 mmol) at about 0° C., and allowed to stir at room temperature for about 12 hours. The reaction mixture was filtered to remove the dicyclohexyl urea and the filtrate was evaporated in vacuo. The residue was purified by silica gel column chromatography using MeOH/$CH_2Cl_2$ (02:98) to isolate the product HPY(490)-NHS Ester (0.331 g, 72%) as a red solid. $^1$H NMR (300 MHz, CDCl$_3$) δ 8.94 (d, J=7.63 Hz, 1H), 8.46 (d, J=1.32 Hz, 1H), 8.38 (d, J=8.07 Hz, 1H) 7.86 (dd, J=9.54, 1.91 Hz, 1H), 7.58-7.54 (m, 2H), 7.49-7.39 (m, 2H), 7.35-7.26 (m, 3H)) 2.91 (s, 4H); $^{13}$C NMR (75 MHz, CDCl$_3$) δ 169.1, 160.2, 155.1, 150.6, 142.53, 142.49, 142.34, 139.2, 133.8, 133.1, 132.93, 132.0, 130.7, 128.9, 128.8, 127.2 (t, J=9.54 Hz, 1C), 120.3, 120.0, 113.3, 108.0, 25.6 (2C); $^{19}$F NMR (300 MHz, CDCl$_3$) 6-149.6 (m, 2F). HRMS/ESI-TOF (m/z): calcd for $[M+H]^+$ $C_{23}H_{16}BF_2N_4O_4$: 461.1133. found: 461.1240.

In an embodiment of the present invention, an amine-reactive N-hydroxysuccinimide ester dye HPY(490)-NHS Ester was synthesized and used to label an antibody for application as a secondary detection reagent.

Figure 2:
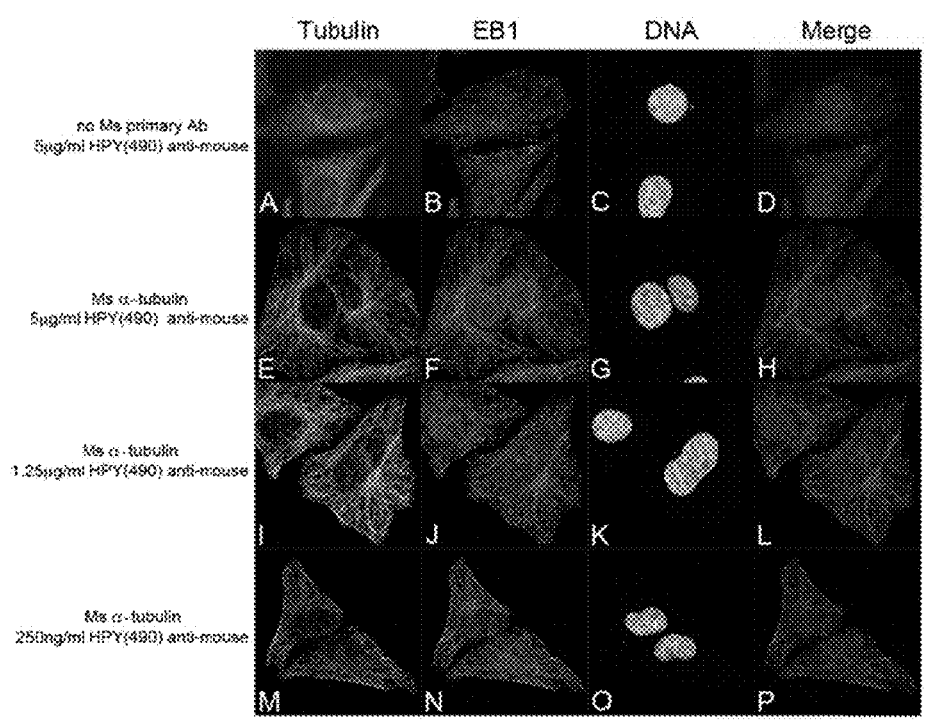
FIG. 2 illustrates the example use of HPY(490) dye conjugated to goat anti-mouse IgG as a secondary detection reagent.

FIG. 2 illustrates use of a HPY(490)-NHS Ester to label a secondary detection reagent. In a non-limiting example, HeLa cells were fixed in about −20° C. MeOH, rehydrated and probed with rabbit anti-EB1 to label to label microtubule cytoskeleton (pseudocolored green), Hoescht 33342 to label DNA, and mouse anti-tubulin (Panels E-P only). Cells were then incubated with varying dilutions of HPY(490)-conjugated goat anti-mouse IgG (Panels A, E, I and M, pseudocolored red).

An example of an antibody labeling procedure with HPY (490)-NHS Ester is as follows. Lyophilized goat anti-mouse IgG (Sigma Co., St. Louis, Mo.) was resuspended in about 0.5 ml phosphate-buffered saline to about 2 mg/ml, and adjusted to pH 8.3 with 1M sodium bicarbonate (final concentration 100 mM). HPY(490)-NHS Ester was resuspended in DMSO, and added to the IgG solution in a 10-fold molar excess. The antibody dye solution was incubated with gentle stirring for an hour at room temperature. The free dye was then separated by gel exclusion column chromatography and the concentration of the IgG as well as the dye:IgG molar ratio was calculated to be approximately 1:1 using a UV-VIS spectrophotometer (Bio-Rad, Hercules, Calif.).

FIG. 2 illustrates the example use of HPY(490)-dye conjugated to goat anti-mouse IgG as an effective secondary detection reagent. The conjugation step was conducted using the standardized buffers and reagents available in commercial protein labeling kits. The HPY(490)-conjugated antibody was separated the from the free dye using standard conditions for gel exclusion column chromatography. The concentration of the antibody and molar ratio of dye to IgG was determined spectrophotometrically to be (1:1). The utility of the secondary antibody on HeLa cells fixed and probed for microtubules with either mouse anti-α tubulin or a rabbit anti-EB1 antibody, which primarily labels microtubule ends. As shown in FIG. 2, in the absence of primary mouse antibody, a low level of non-specific fluorescence could be detected (Panel A). However, in the presence of mouse anti-tubulin (Panels E-P), the HPY490-conjugated anti-mouse antibody was effective at detecting microtubules, even at low concentrations (Panels M-P). These images were collected with a 545/610 filter cube, although the optimal excitation/emission filters would be closer to standard fluorescein filter.

to remove the dicyclohexyl urea and the filtrate was evaporated in vacuo. The residue was purified by silica gel column chromatography using MeOH/CH$_2$Cl$_2$ (05:95) to isolate the product HPY(405)-NHS Ester (0.237 g, 65%) as a yellow solid. $^1$H NMR (300 MHz, CDCl$_3$) δ 8.29 (d, J=1.03 Hz, 1H), 7.68 (dd, J=9.68, 2.05 Hz, 1H), 6.58 (d, J=9.68 Hz, 1H), 2.95-2.84 (m, 4H), 2.04-1.93 (m, 4H); $^{13}$C NMR (75 MHz, CDCl$_3$) δ 179.9, 171.7, 169.2, 159.7, 142.5, 138.0, 112.1, 106.2, 33.1, 31.4, 25.5, 25.3, 25.2, 23.9; $^{19}$F NMR (300 MHz, CDCl$_3$) δ −154.1 (m, 2F); UV-Vis (CH$_2$Cl$_2$) $\lambda_{max}$: 407 nm; = C=22250 M$^{-1}$ cm$^{-1}$; $\lambda_{em}$: 430 nm and 472 nm.

Compound Name: HPY(405)-Carboxylic Acid NHS Ester
Structure I: R$_1$-R$_2$=cyclopentyl, R$_3$, R$_4$, R$_6$=H, R$_5$=carboxy-succinimidyl ester

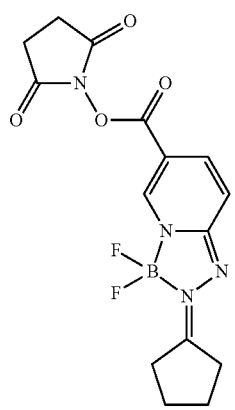

HPY(490)-Carboxylic Acid NHS Ester
Chemical Formula: C$_{15}$H$_{15}$BF$_2$N$_4$O$_4$
Molecular Weight: 364.11
1.6

Compound Name: HPY(530)-Heptynoic Acid NHS Ester
Structure I: R$_1$-R$_2$=fluorene, R$_3$, R$_4$, R$_6$=H, R$_5$=hept-6-ynoic-succinimidyl ester

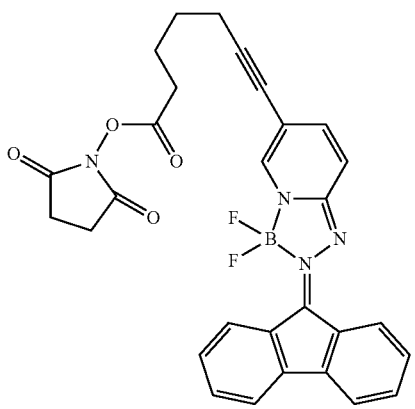

HPY(530)-heptynoic-NHS
Chemical Formula: C$_{29}$H$_{23}$BF$_2$N$_4$O$_4$
Molecular Weight: 540.33
1.7

The HPY(405)-NHS Ester is an amine-reactive activated ester derivative that is effective for coupling with organic amines to form carboxamide linkages as a method of labeling with this fluorescent dye.

The HPY(405)-NHS Ester is an effective labeling agent for organic amines, and other amine-containing biomolecules such as proteins and antibodies. As a reagent this compound exhibits good chemical stability and easily stored for extended periods with exclusion of water. This compound is neutral and very small, and has high relative water solubility, which are advantages for use as labeling agents.

Example: HPY(405)-NHS Ester Chemical synthesis, characterization data, photophysical properties.

To a mixture of HPY(405)-Carboxylic Acid (about 0.267 g, 1 mmol) and N-hydroxysuccinimide (about 0.120 g, 1.05 mmol) in CH$_2$Cl$_2$ (30 mL) was added DCC (about 0.216 g, 1.05 mmol) at about 0° C. and allowed to stir at room temperature for about 12 hours. The reaction mixture was filtered The HPY(530)-Heptynoic Acid NHS Ester has favorable photochemical properties that are directly comparable to the simple HPY(530) structure, and possesses an amine-reactive NHS ester group that is useful for labeling.

This compound and corresponding carboxamide products exhibit an absorption maximum at 530 nm and favorable photochemical properties that are directly comparable with the unsubstituted HPY(530). This structure illustrates the effect of the linkage to the pyridinium ring, here an alkyne, that does not cause a shift in the absorbance and emission spectra that the carboxylic group in the 5-position caused with a "blue-shift" to 490. The HPY(530)-Heptynoic Acid NHS Ester is an effective labeling agent for organic amines, and other amine-containing biomolecules such as proteins and antibodies. This compound is representative of other analogs possessing substitutents with different chain lengths or other functionality to adjust physicochemical properties.

HPY(530)-Heptynoic NHS Ester Chemical synthesis.

A mixture of HPY(530)-Iodide (97 mg, 0.22 mmol), the NHS-ester of 6-heptynoic acid: 2,5-dioxopyrrolidin-1-yl hept-6-ynoate (50 mg, 0.22 mmol), $PdCl_2(PPh_3)_2$ (12 mg, 0.017 mmol), and CuI (3 mg, 0.017 mmol), in dry triethylamine (3 mL) under an argon atmosphere was allowed to stir at room temperature for about 24 hours. The reaction mixture was filtered through celite and the filtrate was evaporated under reduced pressure. The product HPY(530)-Heptynoic NHS Ester was used for subsequent reactions without further purification.

Compound Name: HPY(490)-Hydrazide

Structure I: $R_1$-$R_2$=fluorene, $R_3$, $R_4$, $R_6$=H, $R_5$=hydrazide

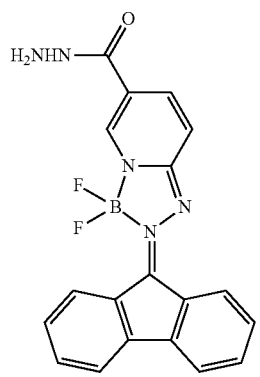

HPY(490)-Carboxylic Acid Hydrazide
Chemical Formula: $C_{19}H_{14}BF_2N_5O$
Molecular Weight: 377.16
1.8

The hydrazide group of HPY(490)-Hydrazide confers physicochemical properties that are useful for fluorescent dyes, and has chemical reactivity that can be used to label organic carbonyl compounds, or the hydrazide can be activated for coupling through diazotization, oxidation or metal-mediated reactions.

The HPY(490)-Hydrazide is relatively small, and has photophysical properties that are directly comparable to the carboxylic acid and other carboxamide derivatives. The hydrazide functional group is useful for many different types of labeling, particularly by coupling the hydrazide group to aldehyde carbonyls.

Example: HPY(490)-Carboxylic Acid Hydrazide Chemical synthesis, characterization data, photophysical properties.

To a solution of HPY(490)-NHS (about 0.018 g, 0.03 mmol) in $CH_2Cl_2$ (about 2 mL) was added anhydrous hydrazine (about 12.2 μL, 0.3 mmol) and allowed to stir at room temperature under an argon atmosphere for about 20 min. Water was added, the precipitate was filtered and dried in vacuo to give the product HPY(490)-Carboxylic Acid Hydrazide (about 0.012 g, 80%) as a red solid. $^1$H NMR (300 MHz, DMSO-$D_6$) δ9.81 (bs, 1H), 8.95 (d, J=6.75 Hz, 1H), 8.40 (bs, 1H), 8.26 (d, J=9.10 Hz, 1H), 8.12 (d, J=9.10 Hz, 1H), 7.91-7.87 (m, 2H), 7.61-7.36 (m, 4H), 7.15 (d, J=9.83 Hz, 1H), 4.15 (bs, 2H); $^{19}$F NMR (300 MHz, DMSO-$D_6$) δ −148.4 (m, 2F); UV-Vis (DMSO) $\lambda_{max}$: 518 nm; $\epsilon$=38700 $M^{-1}$ $cm^{-1}$; $\lambda_{emiss}$=586 nm; $\phi_f$=0.23.

Compound Name: HPY(530)-Propenoic Acid (and derivatives)

Structure I: $R_1$-$R_2$=fluorene, $R_3$, $R_4$, $R_6$=H, $R_5$=prop-2-enoic-tert-butyl ester

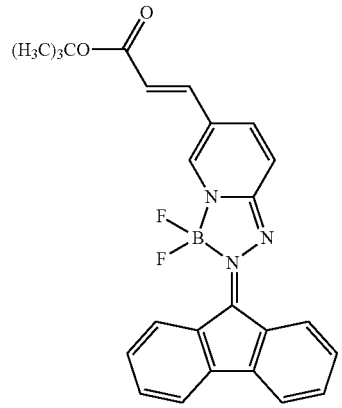

HPY(530)-Propenoic Acid tert-butyl ester
Chemical Formula: $C_{25}H_{22}BF_2N_3O_2$
Molecular Weight: 445.27
1.9

The HPY(530)-Propenoic Acid tert-Butyl Ester (shown) has favorable photochemical properties that are directly comparable to the simple HPY(530) structure, and possesses a protected tert-butyl ester group that can be easily converted to other carboxylic derivatives.

This compound exhibits an absorption maximum at 530 nm and favorable photochemical properties that are directly comparable with the unsubstituted HPY(530). This structure illustrates the important effect of the linkage to the pyridinium ring, here a conjugated alkene, that does not cause a shift in the absorbance and emission spectra that the carboxylic group in the 5-position caused with a "blue-shift" to 490. The HPY(530)-Propenoic Acid tert-Butyl Ester can be used as a precursor for labeling organic amines, and other amine-containing biomolecules such as proteins and antibodies. The conjugated alkene can also be used for chemical reactions to attach other groups, or in cell fixation procedures that involve cross-linking with nucleophilic reagents and cellular components.

Example: HPY(530)-Propenoic Acid tert-Butyl Ester Chemical synthesis, characterization data, photophysical properties.

A mixture of HPY(530)-Iodide (about 0.088 g, $O_2$ mmol) t-butylacrylate (about 0.128 mg, 1 mmol), $Pd(OAc)_2$ (about 0.00134 g, 3 mol %), triphenylphosphine (about 0.0039 g, 7 mol %) and triethylamine (about 60 μL) in dry acetonitrile (about 2 mL) was heated at about 80° C. for about 6 hours. The reaction mixture was filtered through celite and the filtrate was concentrated under reduced pressure. The residue was purified by silica gel column chromatography using $CH_2Cl_2$ to isolate the product HPY(530)-Propenoic Acid tert-Butyl Ester (about 0.055 g, 65%) as a red solid. $^1$H NMR (300 MHz, CDCl$_3$) δ 8.97 (d, J=7.78 Hz, 1H), 8.38 (d, J=7.92 Hz, 1H), 7.66-7.54 (m, 4H), 7.45-7.25 (m, 5H), 6.89 (d, J=9.39 Hz, 1H), 6.15 (d, J=15.85 Hz, 1H), 1.53 (s, 9H); $^{13}$C NMR (75 MHz, CDCl$_3$) 165.9, 160.0, 151.6, 141.9, 141.8, 138.1, 138.2, 137.8, 137.2, 137.1, 132.8, 132.3, 132.1, 131.8, 131.0, 128.6, 128.5, 126.7, 120.1, 119.8, 118.8, 118.0, 114.0, 28.2;

$^{19}$F NMR (300 MHz, CDCl$_3$) δ −150.7 (m, 2F); UV-Vis (Octanol); $λ_{max}$: 547 nm, $\epsilon$=23700 M$^{-1}$ cm$^{-1}$, $λ_{em}$: 591 nm, $\phi_f$=0.50.

Compound Name: HPY(490)-Dioxy-Amine

Structure I: R$_1$-R$_2$=fluorine, R$_3$, R$_4$, R$_6$=H, R$_5$=N-(2-(2-(2-aminoethoxy)ethoxy)ethyl)carboxamide

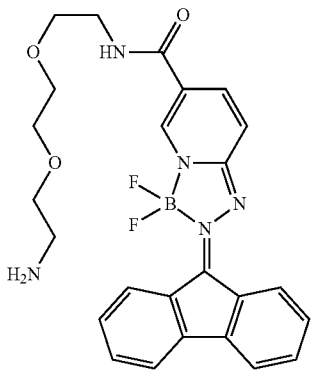

HPY(490)-Dioxy-Amine
Chemical Formula: C$_{25}$H$_{26}$BF$_2$N$_5$O$_3$
Molecular Weight: 493.31
2.0

The HPY(490)-Dioxy-Amine is a carboxamide derivative with a basic amine group, that has favorable physicochemical and photophysical properties for use as a dye, and selectively stains the lysosomes in living cells and is useful for imaging that important cellular organelle.

The HPY(490)-Dioxy-Amine is an excellent dye for imaging lysosomes in living cells, and can be used to label other amine-reactive compounds.

Example: HPY(490)-Dioxy-Amine Chemical synthesis, characterization data, photophysical properties.

To a solution of 2,2'-(ethane-1,2-diylbis(oxy))diethanamine (1.48 g, 1 mmol) in CH$_2$Cl$_2$ (15 mL) was added slowly a solution of HPY(490)-NHS ester in CH$_2$Cl$_2$ (15 mL) at 0° C. and allowed to stir at room temperature for about 20 hours. The reaction mixture was diluted with CH$_2$Cl$_2$ (50 mL) and washed with water (70 mL), brine (50 mL), the organic layer was separated, dried over Na$_2$SO$_4$, and then concentrated in vacuo to isolate the product HPY(490)-Dioxy Amine (0.369 g, 75%) as a red solid. $^1$H NMR (300 MHz, CDCl$_3$) δ 8.88 (d, J=7.78 Hz, 1H), 8.33 (bs, 2H), 7.94-7.91 (m, 1H), 7.69 (bs, 1H), 7.49-7.46 (m, 2H), 7.36-7.19 (m, 4H), 6.80 (d, J=9.39 Hz, 1H), 3.63-3.53 (m, 10H), 2.89 (t, J=4.70 Hz, 2H), 2.54 (bs, 2H); $^{13}$C NMR (75 MHz, CDCl$_3$) δ 164.2, 160.6, 151.6, 141.8, 139.8, 137.1, 132.8, 132.3, 132.1, 131.9, 131.0, 128.6, 128.4, 126.7 (t, J=9.54 Hz, 1C), 120.1, 119.7, 118.0, 112.7, 72.3, 70.3, 69.8, 41.2, 39.8, 29.7 $^{19}$F NMR (300 MHz, CDCl$_3$) δ −150.5 (m, 2F); UV-Vis (EtOH; $λ_{max}$:518 nm, = C=43400 M$^{-1}$ cm$^{-1}$, $\phi_f$=0.61. UV-Vis (octanol) $λ_{max}$: 523 nm, $\epsilon$=30950 M$^{-1}$ cm$^{-1}$, $\phi_f$=0.99. UV-Vis (H$_2$O) $λ_{max}$: 496 nm, = C=18200 M$^{-1}$ cm$^{-1}$; $λ_{em}$: 578 nm; $\phi_f$=0.27. Log P$_{o/w}$=0.70. HRMS/ESI-TOF (m/z): calcd for [M+H]$^+$ C$_{25}$H$_{27}$BF$_2$N$_5$O$_3$: 494.2175. found: 494.2172.

Figure 3:
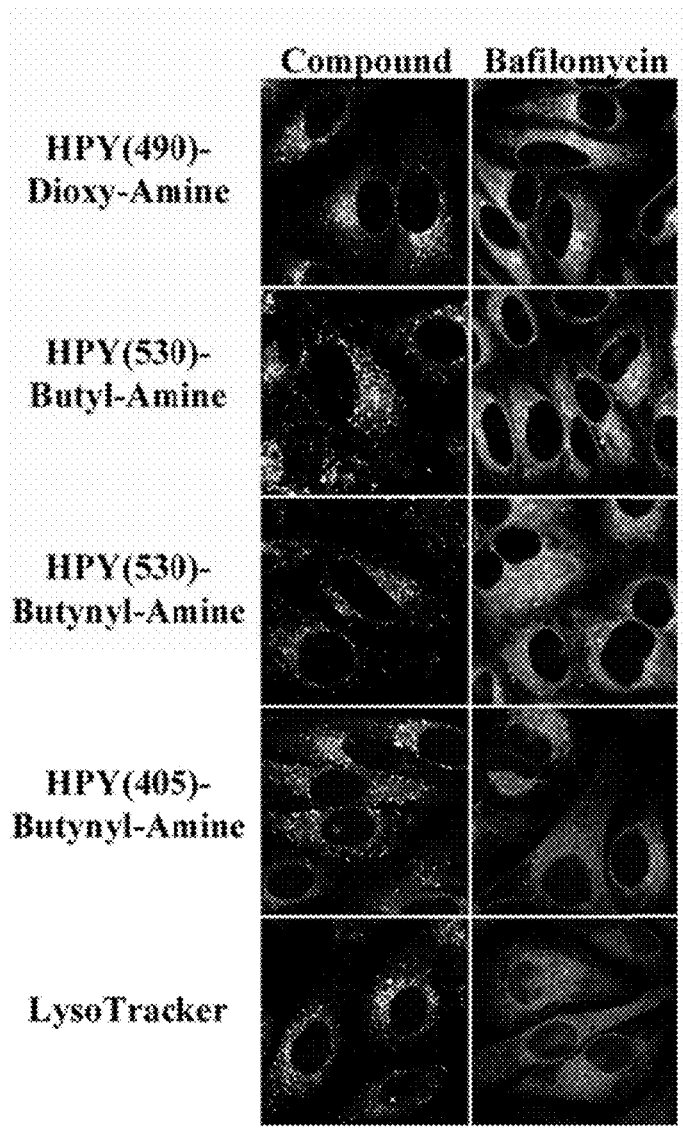
FIG. 3 illustrates an example of HPY-Amine compounds used for lysosome staining.

FIG. 3 illustrates an example of HPY-Amine compounds used for lysosome staining. In this example, HeLa cells were incubated in the absence or presence of 1.0 μM bafilomycin for about 1 hour, then treated with 0.5 μM HPY(490)-Dioxy-Amine, 1.0 μM HPY(530)-Butyl-Amine, 1.0 μM HPY(530)-Butynyl-Amine, 5.0 μM HPY(405)-Butynyl-Amine, or 75 nM LysoTracker for about 30 minutes and imaged live using a 63× objective on a Leica TCS-SP5 II inverted, confocal microscope with resonance scanner. As shown in the right panels, Bafilomycin abrogates lysosomal targeting of HPY-Amine compounds as well as LysoTracker in live HeLa cells.

Use of HPY-Amine compounds for staining lysosomes was conducted in HeLa cells by the following non-limiting example procedure. HeLa cells were seeded in 35 mm glass-bottom FluoroDishes at a density of about 3.0×10$^5$ cells per dish and incubated overnight at about 37° C. and about 5% CO$_2$. Cells were then incubated in the absence or presence of about 1.0 μM bafilomycin diluted in EMEM for about 1 hr at about 37° C. and about 5% CO$_2$. Cells were washed three times with warm phosphate buffered saline then treated with about 0.5 μM HPY(490)-Dioxy-Amine, 1.0 μM HPY(530)-Butyl-Amine, 1.0 μM HPY(530)-Butynyl-Amine, 5.0 μM HPY(405)-Butynyl-Amine, or 75 nM LysoTracker. The compounds were diluted to a stock solution of about 10 mM using DMSO then diluted further to working concentration using EMEM. The compounds in EMEM solution were warmed to about 37° C. before treatments. Media from dishes was removed and replaced with working concentration of compound and allowed to incubate at about 37° C. and about 5% CO$_2$ for about 30 minutes.

FIG. 3 illustrates acidic compartment targeting of HPY-Amine compounds in HeLa cells. The amine compounds readily penetrated the cell membrane and targeted acidic compartments within about 30 minutes of treatment. As demonstrated above, the compound exhibits similar punctated-vesicular bodies as the commercial lysosomal imaging reagent, LysoTracker. All amine compounds and LysoTracker localization was abrogated once the cells were pre-treated with bafilomycin, which is known to neutralize lysosomes by inhibiting Vacuolar-type H+ ATPases and preventing acidification of these compartments. After bafilomycin treatments, the compounds were completely dispersed throughout cytoplasm. Thus, HPY-Amine compounds specifically target late endosomes and lysosomes.

Compound Name: HPY(530)-Butynyl-Amine

Structure I: R$_1$-R$_2$=fluorene, R$_3$, R$_4$, R$_6$=H, R$_5$=but-3-yn-1-amine

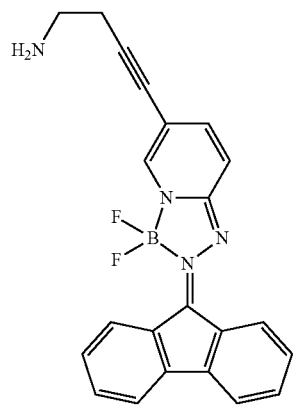

HPY(530)-Butynylamine
Chemical Formula: C$_{22}$H$_{17}$BF$_2$N$_4$
Molecular Weight: 386.20
2.1

The HPY(530)-Butynyl-Amine is a carbon-linked alkyne derivative with a basic amine group, that has favorable physicochemical and photophysical properties for use as a dye, and selectively stains the lysosomes in living cells and is useful for imaging that important cellular organelle.

The HPY(530)-Butynyl-Amine is an excellent dye for imaging lysosomes in living cells, and can be used to label other amine-reactive compounds.

Example: HPY(530)-Butynyl-Amine Chemical synthesis, characterization data, photophysical properties.

Trifluoroacetic acid (0.3 mL) was added slowly to HPY (530)-Butynyl-Amine-$^t$Boc (0.036 g, 0.07 mmol) in CH$_2$Cl$_2$ (0.6 mL) and allowed to stir at room temperature for about 1 hour. The reaction mixture was diluted with CH$_2$Cl$_2$ (4 mL) and neutralized with saturated aqueous NaHCO$_3$ (4 mL) at about 0° C., the organic layer was separated, dried over Na$_2$SO$_4$, and concentrated in vacuo to provide the product HPY(530)-Butynyl-Amine (0.025 g, 90%) as a red solid. $^1$H NMR (300 MHz, CDCl$_3$) δ 8.99 (d, J=7.63 Hz, 1H), 8.39 (d, J=7.78 Hz, 1H), 7.70 (bs, 1H), 7.60-7.56 (m, 2H), 7.47-7.27 (m, 5H), 6.85 (d, J=9.10 Hz, 1H), 2.92 (t, J=6.60 Hz, 2H), 5.54 (t, J=6.46 Hz, 2H), 1.52 (bs, 2H); $^{13}$C NMR (75 MHz, CDCl$_3$) δ 143.6, 141.7, 141.6, 138.7, 132.4, 132.2, 131.9, 131.4, 131.1, 128.5, 128.3, 126.5 (t, J=9.54 Hz, 1H, 1C), 120.0, 119.6, 113.1, 107.5, 89.7, 41.1, 24.5; $^{19}$F NMR (300 MHz, CDCl$_3$) 6-150.8 (q, J=30.34 Hz, 2F); UV-Vis (EtOH) $\lambda_{max:534}$ nm, $\epsilon$=30250 M$^{-1}$ cm$^{-1}$ $\phi_f$=0.13. UV-Vis (octanol) $\lambda_{max}$: 539 nm; $\epsilon$=16430 M$^{-1}$ cm$^{-1}$; $\lambda_{em}$: 587 nm; $\phi_f$=0.43. Log P$_{o/w}$=1.60. HRMS/ESI-TOF (m/z): calcd for [M+H]$^+$ C$_{22}$H$_{18}$BF$_2$N$_4$: 387.1593; found: 387.1588.

As illustrated in FIG. 3, HPY(530)-Butynyl-Amine can be used for lysosome staining.

Compound Name: HPY(530)-Butyl-Amine

Structure I: R$_1$-R$_2$=fluorene, R$_3$, R$_4$, R$_6$=H, R$_5$=but-4-yl-1-amine

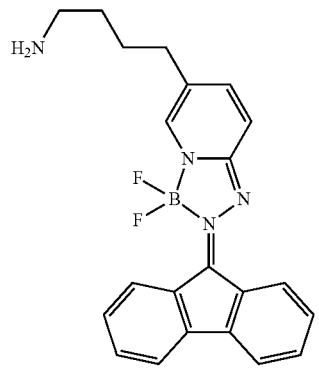

HPY(530)-Butylamine
Chemical Formula: C$_{22}$H$_{21}$BF$_2$N$_4$
Molecular Weight: 390.24
2.2

The HPY(530)-Butyl-Amine is a carbon-linked alkane derivative with a basic amine group, that has favorable physicochemical and photophysical properties for use as a dye, and selectively stains lysosomes in living cells and is useful for imaging that important cellular organelle. The saturated butyl linkage enhances the quantum yield in octanol solvent, relative to the alkyne-linked compound, and has greater chemical resistance to acidic, electrophilic and oxidizing reagents.

The HPY(530)-Butyl-Amine is an excellent dye for imaging lysosomes in living cells, and can be used to label other amine-reactive compounds.

Example: HPY(530)-Butyl-Amine Chemical synthesis, characterization data, photophysical properties.

Trifluoroacetic acid (0.3 mL) was added slowly to HPY (530)-Butyl-Amine-$^t$Boc (0.036 g, 0.07 mmol) in CH$_2$Cl$_2$ (0.6 mL) and allowed to stir at room temperature for about 1 hour. The reaction mixture was diluted with CH$_2$Cl$_2$ (4 mL) and neutralized with saturated aqueous NaHCO$_3$ (4 mL) at about 0° C. The organic layer was separated, dried over Na$_2$SO$_4$, concentrated in vacuo to yield the product (0.025 g, 90%) as a red solid. $^1$H NMR (300 MHz, CDCl$_3$) δ 9.05 (d, J=7.34 Hz, 1H), 8.42 (d, J=7.78 Hz, 1H), 7.63-7.59 (m, 2H), 7.45-7.29 (m, 5H), 6.90 (d, J=9.2 Hz, 1H), 2.75 (t, J=6.90 Hz, 2H), 2.49 (t, J=7.34 Hz, 2H), 1.67-1.46 (m, 6H) $^{19}$F NMR (300 MHz, CDCl$_3$) δ -151.2 (q, J=32.08 Hz, 2F); UV-Vis (octanol) $\lambda_{max}$: 533 nm; $\epsilon$=22522 M$^{-1}$ cm$^{-1}$; $\lambda_{em}$: 575 nm; $\phi_f$=0.52.

As illustrated in FIG. 3, HPY(530)-Butylamine can be used for lysosome staining.

Compound Name: HPY(405)-Butynyl-Amine

Structure I: R$_1$-R$_2$=cyclopentyl, R$_3$, R$_4$, R$_6$=H, R$_5$=but-3-yn-1-amine

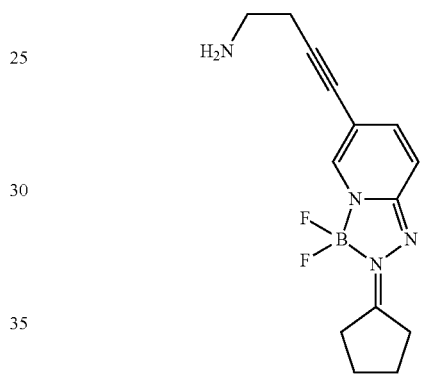

HPY(405)-Butynylamine
Chemical Formula: C$_{14}$H$_{17}$BF$_2$N$_4$
Molecular Weight: 290.12
2.3

The HPY(405)-Butynyl-Amine is a carbon-linked alkane derivative with a basic amine group, that has favorable physicochemical and photophysical properties for use as a dye, and selectively stains the lysosomes in living cells and is useful for imaging that important cellular organelle.

The HPY(405)-Butynyl-Amine is an excellent dye for imaging lysosomes in living cells, and can be used to label other amine-reactive compounds.

Example: HPY(405)-Butynyl-Amine Chemical synthesis, characterization data, photophysical properties.

Trifluoroacetic acid (0.3 mL) was added slowly to HPY (405)-Butynyl-Amine-$^t$Boc (0.036 g, 0.092 mmol) in CH$_2$Cl$_2$ (0.6 mL) and allowed to stir at room temperature for about 1 hour. The reaction mixture was diluted with CH$_2$Cl$_2$ (4 mL) and neutralized with saturated aqueous NaHCO$_3$ (4 mL) at about 0° C. The organic layer was separated, dried over Na$_2$SO$_4$, and concentrated in vacuo to yield the product HPY (405)-Butynyl-Amine (0.018 g, 70%) as a yellow solid. $^1$H NMR (300 MHz, CDCl$_3$): δ 7.47 (s, 1H), 7.22 (dd, J=9.39, 1.90 Hz, 1H), 6.52 (d, J=9.5 Hz, 1H), 2.29-2.78 (m, 6H), 2.51 (t, J=6.31 Hz, 2H), 1.98-1.89 (m, 4H), 1.70 (bs, 2H); $^{19}$F NMR (300 MHz, CDCl$_3$) δ -154.60 (q, J=28.61 Hz, 2F); UV-Vis (octanol; $\lambda_{max}$: 408 nm; $\epsilon$=5290 M$^{-1}$ cm$^{-1}$; $\lambda_{em}$: 455 nm and 485 nm; $\phi_f$=0.51.

As illustrated in FIG. 3, HPY(530)-Butynylamine can be used for lysosome staining.

Compound Name: HPY(405)-Butyl-Amine

Structure I: $R_1$-$R_2$=cyclopentyl, $R_3$, $R_4$, $R_6$=H, $R_5$=but-4-yl-1-amine

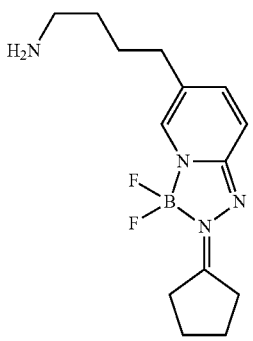

HPY(405)-Butylamine
Chemical Formula: $C_{14}H_{21}BF_2N_4$
Molecular Weight: 294.15
2.4

The HPY(405)-Butynyl-Amine has favorable photophysical and physicochemical properties, and can be used to label other amine-reactive compounds.

Example: HPY(405)-Butynyl-Amine Chemical synthesis, characterization data.

Trifluoroacetic acid (0.3 mL) was added slowly to the HPY(405)-Butyl-Amine-$^t$Boc (0.036, 0.09 mmol) in $CH_2Cl_2$ (0.6 mL) and stirred at room temperature for about 1 hour. The reaction mixture was diluted with $CH_2Cl_2$ (4 mL) and neutralized with saturated aqueous $NaHCO_3$ (4 mL) at about 0° C. The organic layer was separated, dried over $Na_2SO_4$ and concentrated in vacuo to yield the product HPY(405)-Butyl-Amine (0.019 g, 75%) as a viscous oil. $^1$H NMR (300 MHz, $CDCl_3$) δ 7.18-7.14 (m, 2H), 6.56 (d, J=10.2 Hz, 1H), 2.94-2.69 (m, 6H), 2.49-2.24 (m, 4H), 1.96-1.85 (m, 4H), 1.50-1.45 (m, 4H); $^{19}$F NMR (300 MHz, $CDCl_3$) δ −154.81 (q, J=26.88 Hz, 2F).

Compound Name: HPY(405)-Dioxy-Amine-$^t$Boc

Structure I: $R_1$-$R_2$=cyclopentyl, $R_3$, $R_4$, $R_6$=H, $R_5$=N-(2-(2-(2-tert-butyl-carbamylethoxy)ethoxy)ethyl)carboxamide

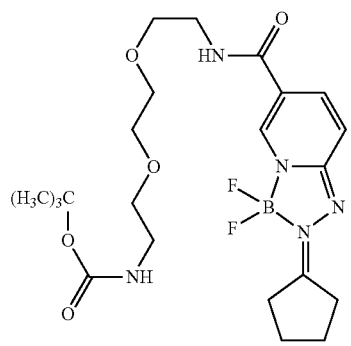

HPY(405)-Dioxy Amine-$^t$Boc
Chemical Formula: $C_{22}H_{34}BF_2N_5O_5$
Molecular Weight: 497.34
2.5

This is a protected amine derivative that can be used for the synthesis of labeled compounds.

This is a very small fluorescent dye with a hydrophilic linkage that confers high water solubility.

Example: HPY(405)-Dioxy-Amine-$^t$Boc Chemical synthesis, characterization data, photophysical properties.

To a solution of tert-butyl 2-(2-(2-aminoethoxy)ethoxy)ethylcarbamate (0.134 g, 0.54 mmol) and triethylamine (90 μL, 0.64 mmol) in $CH_2Cl_2$ (10 mL) was added HPY(405)-NHS (197 mg, 0.54 mmol) in $CH_2Cl_2$ (10 mL) at about 0° C. and stirred at room temperature for about 8 hours. The reaction mixture was diluted with $CH_2Cl_2$ (20 mL) and washed with water (2×30 mL). The organic layer was separated, dried over $Na_2SO_4$ and then concentrated in vacuo. The residue was purified by silica gel column chromatography using MeOH/$CH_2Cl_2$ (02:98) eluent to isolate the product HPY(405)-Dioxy-Amine-$^t$Boc (0.198 g, 74%) as a viscous yellow oil. $^1$H NMR (300 MHz, $CDCl_3$) δ 7.97 (bs, 1H), 7.68 (d, J=8.36 Hz, 1H), 6.64-6.54 (m, 2H), 5.01 (bs, 1H), 3.70-3.54 (m, 10H), 3.36-3.27 (m, 2H), 2.95-2.81 (m, 4H), 1.99-1.87 (m, 5H), 1.43 (bs, 9H); $^{13}$C NMR (75 MHz, $CDCl_3$) δ 176.2, 175.3, 164.4, 160.3, 155.9, 137.9, 136.6, 115.4, 111.3, 79.3, 70.1, 41.7, 40.1, 39.6, 32.7, 31.0, 28.3, 25.3, 23.9; $^{19}$F NMR (300 MHz, $CDCl_3$) −154.25 (q, J=26.87 Hz, 2F); UV-Vis (octanol) $\lambda_{max}$:391 nm; $\varepsilon$=10150 $M^{-1}$ $cm^{-1}$; $\lambda_{em}$: 438 nm and 468 nm; $\phi_f$=0.42. Log $P_{o/w}$=0.955.

Compound Name: HPY(490)-Dioxy-Mitoxy

Structure I: $R_1$-$R_2$=fluorene, $R_3$, $R_4$, $R_6$=H, $R_5$=N-(2-(2-(2-(triphenylphosphonium-3-propanamido)ethoxy)ethoxy)ethyl)carboxamide

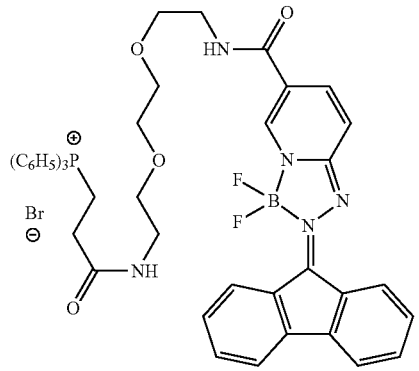

HPY(490)-Dioxy-Mitoxy
Chemical Formula: $C_{46}H_{44}BBrF_2N_5O_4P$
Molecular Weight: 890.56
2.6

The HPY(490)-Dioxy-Mitoxy is a carboxamide derivative with a positively charged phosphonium group, that has favorable physicochemical and photophysical properties for use as a dye, and selectively stains the mitochondria in living cells and is useful for imaging that important cellular organelle.

The HPY(490)-Dioxy-Amine is an excellent dye for imaging mitochondria in living cells.

Example: HPY(490)-Dioxy-Mitoxy Chemical synthesis, characterization data, photophysical properties.

To a mixture of HPY(490)-Dioxy-Amine (0.016 g, 0.0324 mmol) and triethylamine (11.2 μL, 0.081 mmol) in $CH_2Cl_2$ (1 mL), was added a solution of (3-(2,5-dioxopyrrolidin-1-yloxy)-3-oxopropyl)triphenylphosphonium bromide (0.017 g, 0.0324 mmol) in $CH_2Cl_2$ (1 mL) at about 0° C. under an argon atmosphere and allowed to stir at room temperature for about 12 hours. The reaction mixture was diluted with CH$_2$Cl$_2$ (5 mL) and washed with water (15 mL), the organic layer was dried over Na$_2$SO4 and the volatiles were removed in vacuo. The residue was purified by silica gel column chromatography using MeOH/CH$_2$Cl$_2$ (5:95) eluent to isolate the product HPY(490)-Dioxy-Mitoxy (0.01 g, 36%). $^1$H NMR (300 MHz, CDCl$_3$) δ 9.01 (d, J=7.48 Hz, 1H), 8.85 (t, J=5.28 Hz, 1H), 8.52 (s, 1H), 8.41 (t, J=5.28 Hz, 1H), 8.35 (d, J=7.63 Hz, 1H), 8.28 (dd, J=9.5, 1.7 Hz, 1H), 7.77-7.56 (m, 13H), 7.46-7.17 (m, 8H), 6.85 (d, J=9.4 Hz, 1H), 3.73-3.57 (m, 11H), 3.43-3.38 (m, 2H), 2.99-2.79 (m, 3H); $^{19}$F NMR (300 MHz, CDCl$_3$) δ −150.2 (m, 2F); UV-Vis (octanol) $\lambda_{max}$: 523 nm; $\epsilon$=37750 M$^{-1}$ cm$^{-1}$, $\lambda_{em}$: 554 nm; $\phi_f$=0.96. Log P$_{o/w}$=0.36. HRMS/ESI-TOF (m/z): calcd for [M+]$^+$ C$_{46}$H$_{44}$BF$_2$N$_5$O$_4$P: 810.3187. found: 810.3189.

Compound Name: HPY(530)-Butynyl-Mitoxy

Structure I: R$_1$-R$_2$=fluorene, R$_3$, R$_4$, R$_6$=H, R$_5$=but-3-yn-1-triphenylphosphonium-3-propanamide

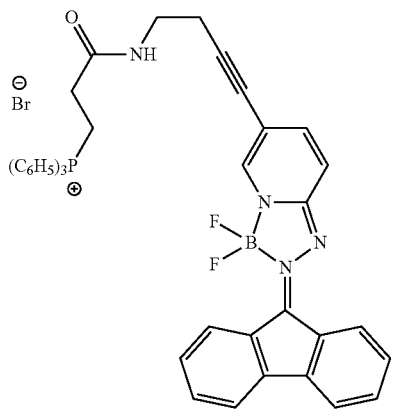

HPY(530)-Butynyl-Mitoxy
Chemical Formula: C$_{43}$H$_{35}$BBrF$_2$N$_4$OP
Molecular Weight: 783.45
2.7

The HPY(530)-Butynyl-Mitoxy is a alkyne-substituted derivative with a positively charged phosphonium group, that has favorable physicochemical and photophysical properties for use as a dye, and selectively stains the mitochondria in living cells and is useful for imaging that important cellular organelle.

The (530)-Butynyl-Mitoxy is an excellent dye for imaging mitochondria in living cells.

Example: HPY(530)-Butynyl-Mitoxy Chemical synthesis, characterization data, photophysical properties.

To a mixture of HPY(530)-Butynyl-Amine (0.022 g, 0.056 mmol) and triethylamine (11.6 µL, 0.084 mmol) in CH$_2$Cl$_2$ (1 mL), was added a solution of (3-(2,5-dioxopyrrolidin-1-yloxy)-3-oxopropyl)triphenylphosphonium bromide (0.017 g, 0.0324 mmol) in CH$_2$Cl$_2$ (1 mL) at about 0° C. under an argon atmosphere and allowed to stir at room temperature for about 3 hours. The reaction mixture was diluted with CH$_2$Cl$_2$ (20 mL) and washed with water (30 mL), the organic layer was separated, dried over Na$_2$SO$_4$, and concentrated in vacuo. The residue was purified by silica gel column chromatography using MeOH/CH$_2$Cl$_2$ (03:95) eluent to isolate the product HPY(530)-Butynyl-Mitoxy (30 mg, 70%) as a red solid. $^1$H NMR (300 MHz, CDCl$_3$) δ 9.07 (t, J=6.6 Hz, 1H), 9.00 (d, J=7.63 Hz, 1H), 8.39 (d, J=8.07 Hz, 1H), 7.85-7.68 (m, 15H), 7.61-7.57 (m, 3H), 7.46-7.26 (m, 4H), 6.82 (d, J=9.39 Hz, 1H), 3.76-3.66 (m, 2H), 3.04-2.95 (m, 2H), 2.64 (t, J=7.04 Hz, 2H).$^{19}$F NMR (300 MHz, CDCl$_3$) δ −150.2 (m, 2F); UV-Vis (octanol; $\lambda_{max}$: 542 nm; $\epsilon$=30750M$^{-1}$ cm$^{-1}$; $\lambda_{em}$: 590 nm; $\phi_f$=0.53. Log P$_{o/w}$=1.06. HRMS/ESI-TOF (m/z): calcd for [M+]$^+$ C$_{43}$H$_{35}$BF$_2$N$_4$OP: 703.2604. found: 703.2604.

Figure 4:
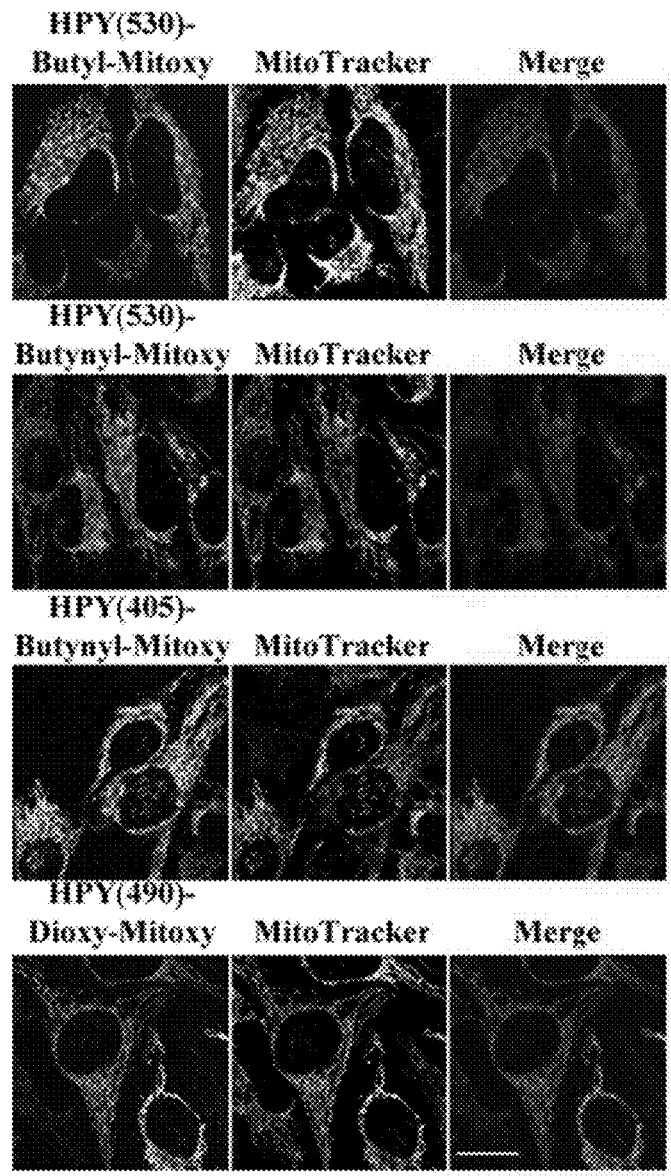
FIG. 4 illustrates HPY-Mitoxy compounds used for mitochondria staining.

FIG. 4 illustrates HPY-Mitoxy compounds for mitochondria staining. Colocalization of HPY-Mitoxy compounds and MitoTracker Deep Red at the mitochondria are shown in live HeLa cells. In this example, HeLa cells were co-treated with 0.8 µM HPY(530)-Butyl-Mitoxy, 0.8 µM HPY(530)-Butynyl-Mitoxy, 5.0 µM HPY(405)-Butynyl-Mitoxy, or 0.8 µM HPY(490)-Dioxy-Mitoxy, and 0.4 µM MitoTracker for about 30 minutes and imaged live using a 63× objective on a Leica TCS-SP5 II inverted, confocal microscope with resonance scanner. Scale bar represents 20 µm.

HeLa cells were seeded in 35 mm glass-bottom FluoroDishes at a density of about 3.0×10$^5$ cells per dish and incubated overnight at about 37° C. and about 5% CO$_2$. Cells were then co-treated with 0.8 µM HPY-(530)-Butyl-Mitoxy, 0.8 µM HPY-(530)-Butynyl-Mitoxy, 0.8 µM HPY-(490)-Dioxy-Mitoxy, or 5.0 µM HPY-(405)-Butynyl-Mitoxy, and 0.4 µM MitoTracker. The compounds were diluted to a stock solution of 10 mM using DMSO then diluted further to the working concentration using EMEM. Compounds in EMEM solution were warmed to about 37° C. before treatments. Media from dishes was removed and replaced with working concentration of compound and allowed to incubate at 37° C. and 5% CO$_2$ for about 30 minutes.

FIG. 4 illustrates HeLa cells treated with HPY-Mitoxy compounds in combination with MitoTracker, a commercially available mitochondria targeting reagent, to evaluate the mitochondria targeting properties of the compound within the cell. The HPY-Mitoxy compounds readily penetrated the cell membrane within about 30 minutes of treatment, and colocalized with MitoTracker at mitochondria tubulovesicular structures. Colocalization between the two compounds demonstrates that HPY-Mitoxy compounds are capable of directly targeting the mitochondria.

Compound Name: HPY(530)-Butyl-Mitoxy

Structure I: R$_1$-R$_2$=fluorene, R$_3$, R$_4$, R$_6$=H, R$_5$=4-butyl-1-triphenylphosphonium-3-propanamide

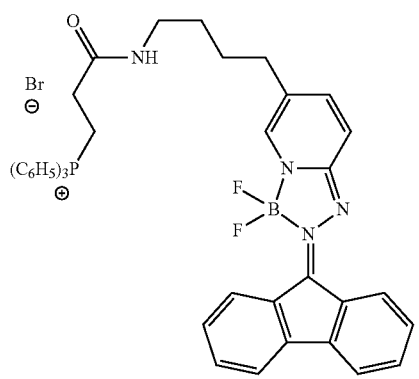

HPY(530)-Butyl-Mitoxy
Chemical Formula: C$_{43}$H$_{39}$BBrF$_2$N$_4$OP
Molecular Weight: 787.48
2.8

The HPY(530)-Butyl-Mitoxy is a saturated alkane-substituted derivative with a positively charged phosphonium group, that has favorable physicochemical and enhanced photophysical properties relative to the butynyl derivative for use as a dye, and selectively stains the mitochondria in living cells and is useful for imaging that important cellular organelle.

The (530)-Butyl-Mitoxy is an excellent dye for imaging mitochondria in living cells.

Example: HPY(530)-Butyl-Mitoxy Chemical synthesis, characterization data, photophysical properties.

To a mixture of HPY(530)-Butyl-Amine (0.03 g, 0.07 mmol) and triethylamine(22 µL, 0.14 mmol) in CH$_2$Cl$_2$ (3 mL) was added, a solution of (3-(2,5-dioxopyrrolidin-1-yloxy)-3-oxopropyl)triphenylphosphonium bromide (0.04 g, 0.078 mmol) in CH$_2$Cl$_2$ (1 mL) at about 0° C. under an argon atmosphere and allowed to stir at room temperature for about 24 hours. The reaction mixture was diluted with CH$_2$Cl$_2$ (25 mL) and washed with water (25 mL), the organic layer was separated, dried over Na$_2$SO$_4$ and concentrated in vacuo. The residue was purified by silica gel column chromatography using MeOH/CH$_2$Cl$_2$ (02:98) eluent to isolate the product HPY(530)-Butyl-Mitoxy (0.05 g, 91%) as a red solid. $^1$H NMR (300 MHz, CDCl$_3$) δ 9.38 (s, 1H), 9.01 (d, J=7.48 Hz, 1H), 8.36 (d, J=7.92 Hz, 1H), 7.80-7.29 (m, 18H), 7.24-7.19 (m, 1H), 6.87 (d, J=8.95 Hz, 1H), 3.78-3.66 (m, 2H), 3.20-3.18 (m, 2H), 2.99-2.88 (m, 2H), 2.52-2.41 (m, 2H); $^{13}$C NMR (75 MHz, CDCl$_3$) δ 169.4, 169.3, 159.9, 147.0, 143.7, 140.9, 135.2, 133.6, 133.5, 132.3, 131.7, 131.6, 130.6, 130.4, 128.3, 128.0, 126.2, 125.9, 119.8, 119.4, 118.1, 117.2, 113.2, 112.3, 39.1, 31.2, 28.9, 28.5, 28.0, 20.6, 20.0; $^{19}$F NMR (300 MHz, DMSO-d$_6$) δ −148.4 (m, 2F); UV-Vis (octanol) λ$_{max}$: 533 nm; ϵ=25200 M$^{-1}$ cm$^{-1}$; λ$_{em}$: 582 nm; ϕ$_f$=0.85. Log P$_{o/w}$=0.99.

FIG. 4 illustrates that HPY(530)-Butyl-Mitoxy can directly target mitochondria in a cell.

Compound Name: HPY(405)-Butynyl-Mitoxy
Structure I: R$_1$-R$_2$=cyclopentyl, R$_3$, R$_4$, R$_6$=H, R$_5$=4-butyl-1-triphenylphosphonium-3-propanamide

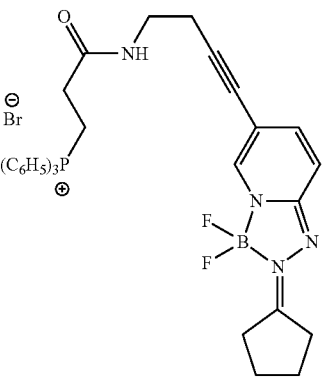

HPY(405)-Butynyl-Mitoxy
Chemical Formula: C$_{35}$H$_{35}$BBrF$_2$N$_4$OP
Molecular Weight: 687.36
2.9

The HPY(405)-Butynyl-Mitoxy is an alkyne-substituted derivative with a positively charged phosphonium group, that has favorable physicochemical and photophysical properties for use as a dye, and selectively stains the mitochondria in living cells and is useful for imaging that important cellular organelle.

The (405)-Butynyl-Mitoxy is very small, has good water solubility, and is an excellent dye for imaging mitochondria in living cells.

Example: HPY(405)-Butynyl-Mitoxy Chemical synthesis, characterization data, photophysical properties.

To a mixture of HPY(405)-Butynyl-Amine (0.036 g, 0.12 mmol) and triethylamine(60 µL, 0.24 mmol) in CH$_2$Cl$_2$ was added a solution of (3-(2,5-dioxopyrrolidin-1-yloxy)-3-oxopropyl)triphenylphosphonium bromide (0.064 g, 0.12 mmol) in CH$_2$Cl$_2$ (1 mL) at 0° C. under an argon atmosphere and allowed to stir at room temperature for about 12 hours. The reaction mixture was diluted with CH$_2$Cl$_2$ (25 mL) and washed with water (25 mL), the organic layer was separated, dried over Na$_2$SO$_4$ and concentrated in vacuo. The residue was purified by silica gel column chromatography using MeOH/CH$_2$Cl$_2$ (05:95) eluent to isolate the product HPY(405)-Butynyl-Mitoxy (0.057 g, 70%) as a yellow solid. $^1$H NMR (300 MHz, CDCl$_3$) δ 9.41 (bs, 1H), 7.77-7.60 (m, 14H), 7.35 (bs, 1H), 7.23 (dd, J=9.39, 1.26 Hz, 1H), 6.42 (d, J=9.24 Hz, 1H), 3.75-3.66 (m, 2H), 3.33-3.26 (m, 2H), 2.91-2.74 (m, 5H), 2.52 (t, J=7.63, 2H), 1.89-1.81 (m, 4H); $^{13}$C NMR (75 MHz, CDCl$_3$) δ 173.9, 169.7, 167.5, 142.8, 138.0, 135.3, 133.8, 133.6, 130.7, 130.5, 118.2, 117.1, 111.6, 105.1, 88.0, 66.2, 38.7, 32.6, 30.9, 29.1, 25.4, 24.0, 20.8, 20.2, 20.1; $^{19}$F NMR (300 MHz, CDCl$_3$) δ −153.4 (m, 2F). UV-Vis (octanol) λ$_{max}$:409 nm; ϵ=8200 M$^{-1}$ cm$^{-1}$; λ$_{em}$: 455 nm and 487 nm; ϕ$_f$=0.47.

FIG. 4 illustrates that HPY(405)-Butynyl-Mitoxy can directly target mitochondria in a cell.

Compound Name: HPY(530)-Heptynoic Azide
Structure I: R$_1$-R$_2$=fluorene, R$_3$, R$_4$, R$_6$=H, R$_5$=N-(2-(2-(2-(2-azidoethoxy)ethoxy)ethoxy)ethyl)hept-6-ynoic-carboxamide

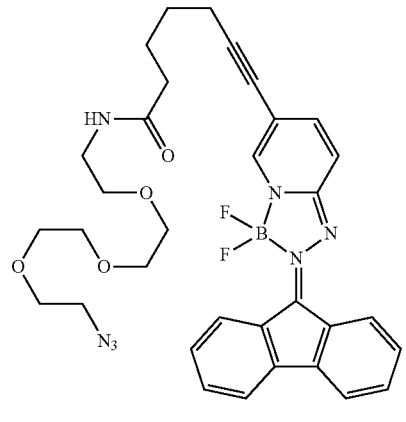

HPY(530)-Heptynoic-Azide
Chemical Formula: C$_{33}$H$_{36}$BF$_2$N$_7$O$_4$
Molecular Weight: 643.49
3.0

The HPY(530)-Heptynoic Azide has favorable photochemical properties that are directly comparable to the simple HPY(530) structure, and possesses an alkyne-reactive azide group that is useful for labeling using the copper(I) catalyzed Huisgen [2+3]cycloaddition reaction (Click reaction).

This compound exhibits an absorption maximum at 530 nm and favorable photochemical properties that are directly comparable with the unsubstituted HPY(530). This structure illustrates the important effect of the linkage to the pyridinium ring, here an alkyne, that does not cause a shift in the absorbance and emission spectra that the carboxylic group in the 5-position caused with a "blue-shift" to 490. The HPY(530)-Heptynoic Azide is an effective labeling agent for the ethynyl-2-deoxy-uridine assay used to detect DNA synthesis. This compound is representative of other analogs possessing substitutents with different chain lengths or other functionality to adjust physicochemical properties.

Example: HPY(530)-Heptynoic Azide Chemical synthesis, characterization data, photophysical properties.

To a mixture of 2-(2-(2-(2-azidoethoxy)ethoxy)ethoxy) ethanamine (0.047 g, 0.22 mmol) and triethylamine (60 µL, 0.44 mmol) in CH$_2$Cl$_2$ (10 mL) was added slowly a solution of HPY(530)-Heptynoic NHS Ester in CH$_2$Cl$_2$ (5 mL) at 0° C. and allowed to stir at room temperature for about 24 hours. The reaction mixture was diluted with CH$_2$Cl$_2$ (25 mL), washed with water (25 mL), the organic layer was separated, dried over Na$_2$SO$_4$ and evaporated in vacuo. The residue was purified by silica gel column chromatography using MeOH/CH$_2$Cl$_2$ (01:99) eluent to isolate the product HPY(530)-Heptynoic Azide (0.074 g, 52%) as a red solid. $^1$H NMR (300 MHz, CDCl$_3$) δ 7.98 (d, J=7.34 Hz, 1H), 8.38 (d, J=7.92 Hz, 1H), 7.70-7.24 (m, 8H), 6.82 (d, J=8.95 Hz, 1H), 6.12 (bs, 1H), 3.74-3.38 (m, 16H), 2.41 (t, J=7.04 Hz, 2H), 2.29-2.16 (m, 2H), 1.85-1.57 (m, 4H); $^{13}$C NMR (75 MHz, CDCl$_3$) δ 172.6, 158.9, 149.9, 143.7, 141.5, 138.4, 131.9, 131.3, 128.4, 126.3, 119.9, 119.6, 113.0, 107.9, 91.5, 72.4, 70.5, 70.1, 69.9, 61.6, 41.9, 40.0, 39.1, 35.9, 33.4, 32.4, 29.5, 28.1, 24.8, 24.1, 19.1; $^{19}$F NMR (300 MHz, CDCl$_3$)-150.7 (m, 2F); IR(Neat) 2100 cm$^{-1}$; UV-Vis (octanol) $\lambda_{max}$: 542 nm; $\epsilon$=24960 M$^{-1}$ cm$^{-1}$; $\lambda_{em}$: 589 nm; $\phi_f$=0.63. UV-Vis (H$_2$O) $\lambda_{max}$: 535 nm; $\epsilon$=22500 M$^{-1}$ cm$^{-1}$; $\lambda_{em}$: 598 nm; $\phi_f$=0.07. Log P$_{o/w}$=1.24.

Figure 5:
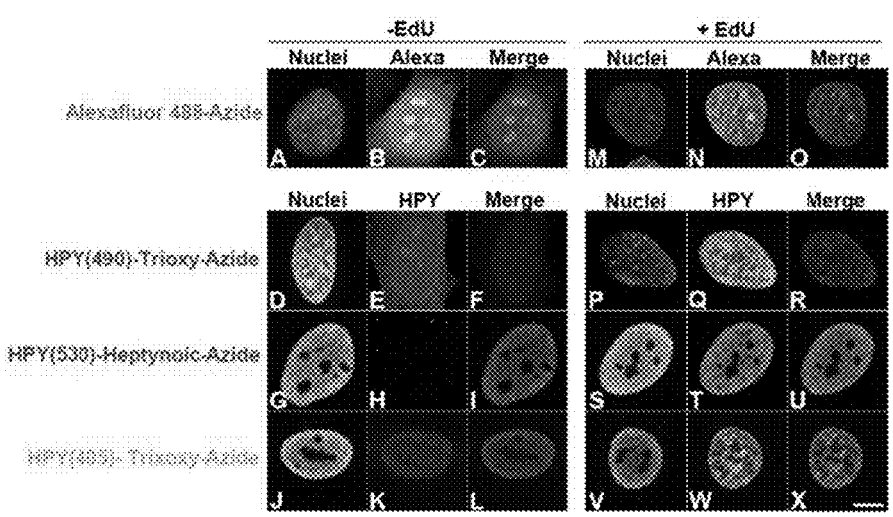
FIG. 5 illustrates an example of a Click-iT EdU assay using HPY-Azide compounds for proliferating HeLa cells.

FIG. 5 is an example of a Click-iT EdU assay using HPY-Azide compounds for proliferating HeLa cells. In this example, HeLa cells were treated with 0.1% DMSO (carrier control, panel A-L) and 10 µM EdU for about 6 hours (panel M-X). Cells were then fixed, permeabilized and treated with Click-iT reaction cocktail containing Alexafluor 488 azide (positive control, panel A-C, M-O), HPY(490)-Trioxy-Azide (panel, D-F, P-R), HPY(530)-Heptynoic-Azide (panel, G-I, S-U) and HPY(405)-Trioxy-Azide (panel, J-L, V-X) individually for 30 mins. Cells were then counter stained for nuclei using either Hoescht 33342 (Panels A-F, M-R) or Acetyl-K9-Histone H3 (G-L, S-X).

In this non-limiting example, HeLa cells were cultured in EMEM media (Lonza, Walkersville, Md.) supplemented with 10% fetal calf serum (Atlanta Biologicals, Lawrenceville, Ga.) sodium pyruvate and sodium bicarbonate. The cultured cells were washed with 1×PBS and treated with 0.1% DMSO (carrier control) and 10 µM EdU prepared in HeLa cell media followed by incubation for six hours. Further, the cells were washed two times with 1×PBS, fixed in 3.7% formaldehyde solution, permeabilized by 0.5% TritonX-100 and thereafter incubated overnight at 4° C. in 1×PBS.

Cells in PBS were then stained with about 0.5 ml of reaction Click-iT reaction cocktail for about 30 minutes using Alexafluor 488 Azide as positive control and HPY-Azide compounds as treatment. Click-iT reaction cocktail was prepared by mixing 1.8 ml of 1XClick-iT reaction buffer, about 80 µl of CuSO$_4$ (Component H), about 5 µl of Alexafluor 488 azide/or HPY-Azide compounds and 200 µl of reaction buffer additive (Invitrogen). Cells were then counterstained for nuclei for about 30 minutes and then mounted in 90% glycerol. Finally, cells were imaged on a Zeiss Axiovert 200M-inverted Microscope equipped with epifluorescence optics and an Apotome structured illumination module (Carl Zeiss, Thornwood, N.Y.).

FIG. 5 demonstrates that the HPY azide compounds can be used as Click labeling reagents to label alkyne groups. In proliferating HeLa cells treated with the nucleoside analog ethynyl-2'-deoxyuridine (EdU) prior to fixation, the azide fluorophores labeled EdU-incorporated DNA, whereas in cells not treated with EdU (-EdU, Left Panels), no specific labeling was observed. The commercially available Alexa Fluor azide (Panels A-C, M-O) was included for comparison.

Compound Name: HPY(490)-Trioxy-Azide
Structure I: $R_1$-$R_2$=fluorene, $R_3$, $R_4$, $R_6$=H, $R_5$=N-(2-(2-(2-(2-azidoethoxy)ethoxy)ethoxy)ethyl)carboxamide

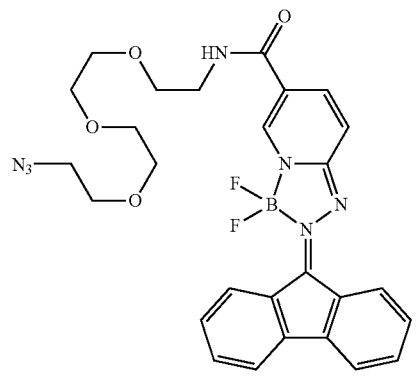

HPY(490)-Trioxy-Azide
Chemical Formula: C$_{27}$H$_{28}$BF$_2$N$_7$O$_4$
Molecular Weight: 563.36
3.1

The HPY(490)-Trioxy Azide has favorable photochemical properties that are directly comparable to the related carboxylic acid and carboxamide derivatives, and possesses an alkyne-reactive azide group that is useful for labeling using the copper(I) catalyzed Huisgen [2+3]cycloaddition reaction (Click reaction).

This compound exhibits an absorption maximum at 490 nm and favorable photochemical properties associated with related derivatives possessing a carboxylic group in the 5-position that produces a "blue-shift" in the absorbance to 490. The HPY(490)-Trioxy Azide is an effective labeling agent for the ethynyl-2-deoxy-uridine assay used to detect DNA synthesis. This compound is representative of other analogs possessing substitutents with different chain lengths or other functionality to adjust physicochemical properties.

Example: Chemical Synthesis, Characterization Data, Photophysical Properties.

To a mixture of 2-(2-(2-(2-azidoethoxy)ethoxy)ethoxy) ethanamine (0.036 g, 0.16 mmol) and triethylamine(42 µL, 0.3 mmol) in CH$_2$Cl$_2$ (8 mL) was slowly added a solution of HPY(490)-NHS Ester (0.069 g, 0.15 mmol) in CH$_2$Cl$_2$ (3 mL) at 0° C. and allowed to stir at room temperature for about 24 hours. The reaction mixture was diluted with CH$_2$Cl$_2$ (25 mL), washed with water (25 mL), the organic layer was separated, dried over Na$_2$SO$_4$ and concentrated in vacuo. The residue was purified by silica gel column chromatography using MeOH/CH$_2$Cl$_2$ (01:99) eluent to isolate the product (0.070 g, 93%) as a red solid. $^1$HNMR (300 MHz, CDCl$_3$) δ8.97 (d, J=7.63 Hz, 1H), 8.38 (d, J=7.78 Hz, 1H), 8.19 (bs, 1H), 7.89 (dd, J=9.39, 2.05 Hz, 1H), 7.57 (d, J=3.08 Hz, 1H), 7.53 (d, J=2.93 Hz, 1H), 7.44-7.24 (m, 4H), 6.87 (d, J=9.39 Hz, 1H), 6.82 (t, J=5.28 Hz, 1H), 3.73-3.63 (m, 14H), 3.36 (t, J=5.15 Hz, 2H); $^{13}$C NMR (75 MHz, CDCl$_3$) δ 164.0, 160.5, 151.7, 141.8, 139.5, 136.8, 132.7, 132.3, 132.0, 131.8, 130.9, 128.6, 128.3, 126.6 (t, J=9.65 Hz, 1C), 120.0, 119.6, 118.0, 112.7, 70.6, 70.4, 70.1, 69.9, 69.6, 50.6, 29.8; $^{19}$F NMR (300

MHz, CDCl$_3$) δ −150.3 (m, 2F). HRMS/ESI-TOF (m/z): calcd for [M+H]$^+$ C$_{27}$H$_{29}$BF$_2$N$_7$O$_4$: 564.2332. found: 564.2338.

FIG. 5 demonstrates that HPY(490)-Trioxy-Azide can be used as Click labeling reagent to label alkyne groups.

Compound Name: HPY(405)-Trioxy-Azide

Structure I: R$_1$-R$_2$=cyclopentyl, R$_3$, R$_4$, R$_6$=H, R$_5$=N-(2-(2-(2-(2-azidoethoxy)ethoxy)ethoxy)ethyl)carboxamide

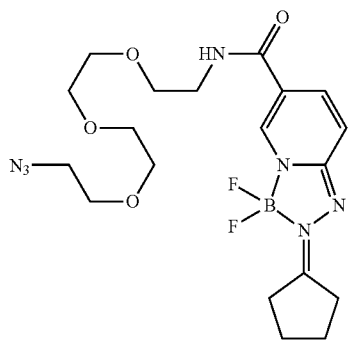

HPY(405)-Trioxy-Azide
Chemical Formula: C$_{19}$H$_{28}$BF$_2$N$_7$O$_4$
Molecular Weight: 467.28
3.2

The HPY(405)-Trioxy Azide has favorable photochemical properties that are directly comparable to the related carboxylic acid and carboxamide derivatives, and possesses an alkyne-reactive azide group that is useful for labeling using the copper(I) catalyzed Huisgen [2+3] cycloaddition reaction (Click reaction).

The HPY(405)-Trioxy Azide has an absorption maximum at 405 nm and favorable photochemical properties, and is an effective labeling agent for the ethynyl-2-deoxy-uridine assay used to detect DNA synthesis. This compound is representative of other analogs possessing substitutents with different chain lengths or other functionality to adjust physicochemical properties.

Example: HPY(405)-Trioxy-Azide Chemical synthesis, characterization data, photophysical properties.

To a mixture of 2-(2-(2-(2-azidoethoxy)ethoxy)ethoxy)ethanamine (0.024 g, 0.11 mmol) and triethylamine(20 μL, 0.2 mmol) in CH$_2$Cl$_2$ (2 mL) was slowly added a solution of HPY(405)-NHS Ester (0.036 g, 0.1 mmol) in CH$_2$Cl$_2$ (2 mL) at 0° C. and allowed to stir at room temperature for about 24 hours. The reaction mixture was diluted with CH$_2$Cl$_2$ (25 mL), washed with water (25 mL, the organic layer was separated, dried over Na$_2$SO$_4$, and econcentrated in vacuo. The residue was purified by silica gel column chromatography using MeOH/CH$_2$Cl$_2$ (02:98) eluent to isolate the product HPY(405)-Trioxy-Azide (0.070 g, 86%) as a yellow solid. $^1$H NMR (300 MHz, CDCl$_3$) δ 7.91 (bs, 1H), 7.63 (dd, J=9.54, 2.05 Hz, 1H) 6.69 (bs, 1H), 6.51 (d, J=9.39 Hz, 1H), 3.62-3.53 (m, 12H), 3.30 (t, J=5.58 Hz, 2H), 2.89-2.73 (m, 4H), 1.95-1.84 (m, 4H); $^{13}$C NMR (75 MHz, CDCl$_3$) δ 194.2, 176.1, 164.3, 160.5, 138.1, 136.5, 115.5, 111.5, 70.6, 70.5, 70.2, 69.9, 69.7, 50.6, 39.7, 32.8, 31.1, 25.3, 24.0; $^{19}$F NMR (300 MHz, CDCl$_3$) δ −154.25 (q, J=30.30 Hz, 2F).

FIG. 5 demonstrates that HPY(405)-Trioxy-Azide can be used as a Click labeling reagent to label alkyne groups.

Compound Name: HPY(405a)-Butynyl-MSTLC

Structure I: R$_1$, R$_2$=methyl, R$_3$, R$_4$, R$_6$=H, R$_5$=[(2R)-2-amino-3-[[(4-methoxyphenyl)diphenylmethyl]thio]-N-[4-[3-butyn-1-yl]propanamide

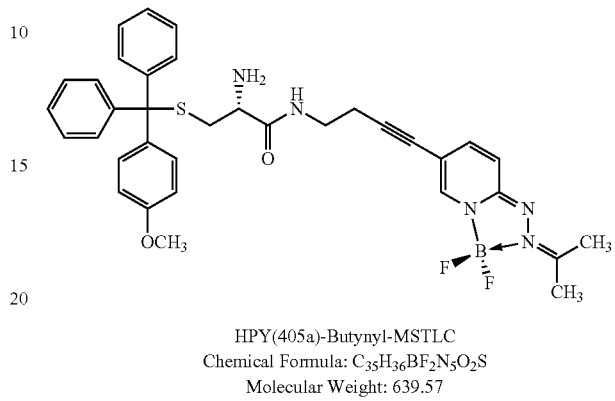

HPY(405a)-Butynyl-MSTLC
Chemical Formula: C$_{35}$H$_{36}$BF$_2$N$_5$O$_2$S
Molecular Weight: 639.57
3.3

The HPY(405a)-Butynyl-MSTLC is a carboxamide conjugate with a biologically active synthetic derivative of S-trityl-L-cysteine that functions as a chemical inhibitor of the kinesin spindle protein KSP (also known as Eg5), and has anticancer properties. This compound is a functional optical probe that combines the capacity for fluorescence with a biologically active compound or "drug."

This compound demonstrates that it is possible to label a biologically active small molecule or drug with an HPY dye, and maintain both the biological activity and the cellular uptake and/or transport that delivers the conjugate to the intracellular target. This compound is representative of the general approach for labeling biologically active compounds with HPY dyes to create functional probes and imaging agents.

Example: HPY(405a)-Butynyl-MSTLC Chemical synthesis, characterization data, photophysical properties.

The product HPY(405a)-Butynyl-MSTLC was synthesized in about 86% yield following the published procedure: Hapuarachchige S, Montano G, Ramesh C, Rodriguez D, Henson L H, Williams C C, Kadavakkollu S, Johnson D L, Shuster C B, Arterburn J B. Design and Synthesis of a New Class of Membrane-Permeable Triazaborolopyridinium Fluorescent Probes. *J Am Chem. Soc.* 2011, 133, 6780-6790. $^1$H NMR (300 MHz, CDCl$_3$): δd 7.45-7.28 (m, 10H), 7.23-7.14 (m, 4H), 6.81 (d, J=9.10 Hz, 2H), 6.48 (d, J=9.39 Hz, 1H), 3.78 (s, 3H), 3.76 (m, 1H), 3.43-3.28 (m, 2H), 3.06 (dd, J=8.37, 3.96 Hz, 1H), 2.74 (dd, J=12.60, 4.02 Hz, 1H), 2.62-2.50 (m, 3H), 2.42 (s, 3H), 2.37 (s, 3H), 1.60 (b s, 2H). $^{13}$C NMR (75 MHz, CDCl$_3$): δd 172.9, 163.1, 158.7, 158.2, 144.9, 144.7, 142.2, 138.2, 136.6, 130.7, 129.5, 127.9, 126.7, 113.2, 111.8, 104.3, 87.2, 77.9, 66.5, 55.2, 54.0, 37.9, 37.3, 21.5, 20.4. $^{19}$F NMR (CDCl$_3$): δ−149.88 (q, J=28 Hz, 2F). FT-IR (Neat): 3360 (b), 2120 (w), 1680 (m), 1510 (m), 1110 (m) cm$^{-1}$. HRMS/ESI-TOF (m/z): calcd for C$_{35}$H$_{36}$BF$_2$N$_5$NaO$_2$S (M+Na) 662.2543. found 662.2543 (M+Na)$^+$.

Compound Name: E2-HPY(530)
Structure I: $R_1$-$R_2$=fluorene, $R_3$, $R_4$, $R_6$=H, $R_5$=17-ethynyl-estra-1,3,5(10)-triene-3,17-diol

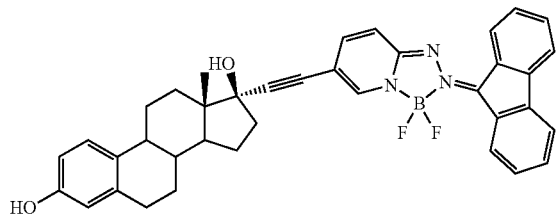

E2-HPY(530)
Chemical Formula: $C_{38}H_{34}BF_2N_3O_2$
Molecular Weight: 613.50
3.4

The E2-HPY(530) is an alkyne conjugate with a biologically active steroid hormone estradiol. This compound is a functional optical probe that combines the capacity for fluorescence while also preserving the biological activity of the original hormone.

This compound demonstrates that it is possible to label a biologically active hormone or drug with a HPY dye, and maintain both the biological activity and the cellular uptake and/or transport that delivers the conjugate to the intracellular target. This compound is representative of the general approach for labeling biologically active compounds with HPY dyes to create functional probes and imaging agents.

Example: E2-HPY(530) Chemical synthesis, characterization data, photophysical properties.

A mixture of HPY(530)-Iodide [2-(9H-fluoren-9-ylidene)-3,3-difluoro-6-iodo-2,3-dihydro-[1,2,4,3]triazaborolo[4,5-a]pyridin-2-ium-3-uide] (30 mg, 0.070 mmol), 17-α-ethynylestradiol (24 mg, 0.08 mmol), $PdCl_2(PPh_3)_2$ (2.35 mg, $3.5 \times 10^{-3}$ mmol) and CuI (0.6 mg, $3.5 \times 10^{-3}$ mmol) in $Et_3N$ (1.5 mL) and NMP (0.5 mL) was stirred at room temperature under a nitrogen atmosphere for about one hour. The reaction mixture was dissolved in methylene chloride, filtered through celite and the volatiles were removed in vacuo. The residue was purified by silica gel column chromatography eluting with 20-35% EtOAc/hexanes to isolate the product E2-HPY (530) (0.039 g, 95%) as a red solid. $^1$H NMR (300 MHz, $CDCl_3$): δ 8.98 (d, J=7.48 Hz, 1H), 8.38 (d, J=7.92, 1H), 7.74 (d, J=0.88 Hz, 1H), 7.60-7.55 (m, 2H), 7.49-7.27 (m, 5H), 7.18 (d, J=8.36 Hz, 1H), 6.84 (d, J=9.39 Hz, 1H), 6.63 (dd, J=8.36, 2.64 Hz, 1H), 6.56 (d, J=2.79 Hz, 1H), 4.60 (s, 1H), 2.86-2.81 (m, 2H), 2.44-2.35 (m, 2H), 2.34 (d, J=11.74 Hz, 1H), 2.10 (dd, J=11.59, 3.52 Hz, 1H), 1.91-1.67 (m, 5H), 1.57-1.36 (m, 5H), 0.93 (s, 3H). $^{13}$C NMR (75 MHz, $CDCl_3$): δ 153.3, 143.5, 141.8, 141.7, 139.1, 139.0, 138.3, 132.7, 132.6, 132.1, 131.7, 128.6, 128.5, 126.6, 120.1, 119.8, 115.2, 113.3, 112.7, 106.7, 94.5, 81.6, 80.5, 49.9, 47.6, 43.6, 39.5, 39.2, 33.2, 29.6, 27.2, 26.4, 22.9, 12.9; UV-Vis (octanol) $\lambda_{max}$: 543 nm; $\epsilon$=24550 $M^{-1}$ $cm^{-1}$; $\lambda_{em}$: 590 nm; $\phi_f$=0.46. Log $P_{o/w}$=0.668.

Metal-mediated coupling strategies have been previously used to incorporate chelates derived from the pyridin-2-yl hydrazine core into estrogen derivatives for the development of $^{99m}$Tc-imaging agents. Thus, an embodiment of the present invention comprises the development of fluorescent dyes based on this scaffold. Hydrazines are versatile reagents in organic and aqueous media with rapid kinetics and favorable thermodynamics of hydrazone formation that are advantageous for bioorthogonol coupling strategies. SoluLink® offers proprietary technologies for bioconjugation using hydrazone formation with hydrazinylnicotinamide groups to connect proteins, DNA, antibodies and solid surfaces. The UV-traceable bis-aryl hydrazone chromophore provides the basis for quantitative determination of protein labeling, but this moiety is not fluorescent. Considering the versatile coupling chemistries associated with pyridin-2-yl-hydrazines and the extended π-systems resulting from hydrazone formation, new fluorescent derivatives were constructed. Embodiments of the present invention comprise a new class of fluorescent hydrazinylpyridine (HPY) dyes incorporating a rigid triazaborolopyridinium core structure as cell permeable imaging probes.

The fluorescent HPY core is structurally related to the widely used BODIPY dyes but provides complementary structural and physicochemical properties, increased hydrophilicity, and efficient emission characterized by large Stokes shifts that avoids self-quenching. The photophysical properties of the HPY dyes are relatively insensitive to varying solvents from non-polar organic to aqueous media, which is complementary to highly environment-sensitive organic dyes such as 4-nitrobenz-2-oxa-1,3-diazole (NBD). A variety of methods are available for the construction of HPY-conjugates that include, but are not limited to, attachment through the hydrazone linkage, or substitutions on the pyridyl ring as represented by the alkyne derivative HPY5 and triazole HPY6 generated by Sonogashira coupling and 1,3-dipolar "click" cyclization chemistry respectively. The HPY series demonstrated tunable absorption/emission properties with substitutions on the pyridyl ring, hydrazone and the groups attached to boron.

In an embodiment of the present invention, a fluorescent estrogen conjugate E2-HPY(530) was synthesized and evaluated for estrogenic properties in different cellular assays. This compound was synthesized by the following procedure.

Data shown in this non-limiting example indicates that in all biological endpoints tested, E2-HPY(530) treatment resulted in similar cellular and subcellular dynamics when compared to the steroid hormone 17-β-estradiol (E2) treatment. These endpoints represent well-characterized cellular (proliferation), transcriptional/nuclear (Invitrogen SelectScreen, RT-PCR), and non-genomic (accumulation of phospho-ERK) effects of E2 stimulation. Computational docking studies demonstrate that E2-HPY(530) is able to fit within the protein structure of the estrogen receptor ERα.

Figure 6:
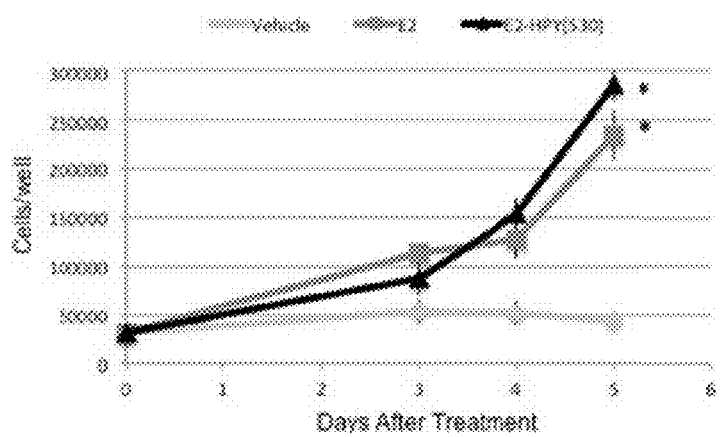
FIG. 6 illustrates a graph showing E2-HPY(530) treatment increasing MCF7 cell proliferation and growth curve analysis of MCF7 breast cancer cells proliferation after treatment 10 nM E2, nM E2-HPY(530), or vehicle (ethanol)

FIG. 6 illustrates the estrogenic potential of E2-HPY(530) in MCF7 cells. E2-HPY(530) increases the proliferation of MCF7 and is statistically indistinguishable from E2-induced MCF7 breast cancer cell proliferation. MCF7 cells ($1 \times 10^4$) were seeded in 24 well plates and grown for about 24 hours. Cell were treated with 10 nM E2, 10 nM E2-HPY(530), or vehicle (ethanol) in phenol red-free DMEM containing 10% charcoal-stripped FBS after washing twice with PBS. Cells were collected after trypsin treatment and counted using a hemocytometer on the indicated day after treatment.

As illustrated in FIG. 6, E2-HPY(530) treatment increases MCF7 cell proliferation. Growth curve analysis of MCF7 breast cancer cell proliferation after treatment 10 nM E2, 10 nM E2-HPY(530), or vehicle (ethanol). Individual treatments were performed in triplicate and data represent the mean values of three independent experiments. Error bars represent the standard error of the mean (SEM). * is statistically different from vehicle treatment p<0.05.

Figure 7:
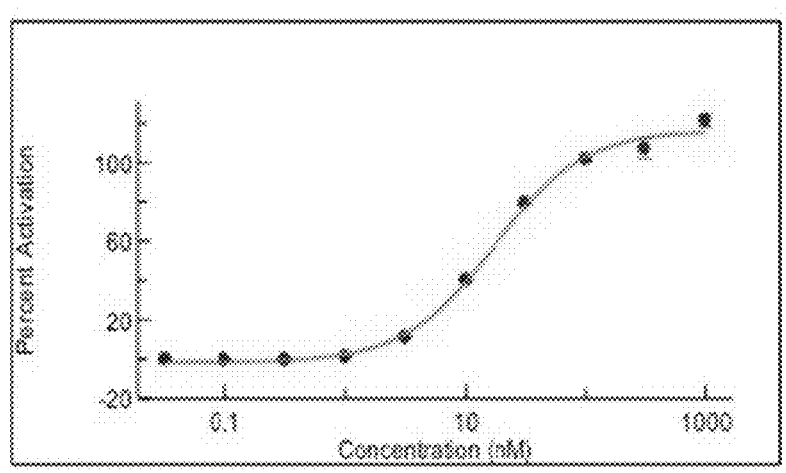
FIG. 7 illustrates a graph showing E2-HPY(530) treatment inducing ER-mediated transcription.

FIG. 7 illustrates that E2-HPY(530) induces the transcription of an estrogen receptor (ER)-dependent promoter. E2-HPY(530) was provided to Invitrogen and these data were obtained via Invitrogen's SelectScreen® Profiling Service.

Figure 15:
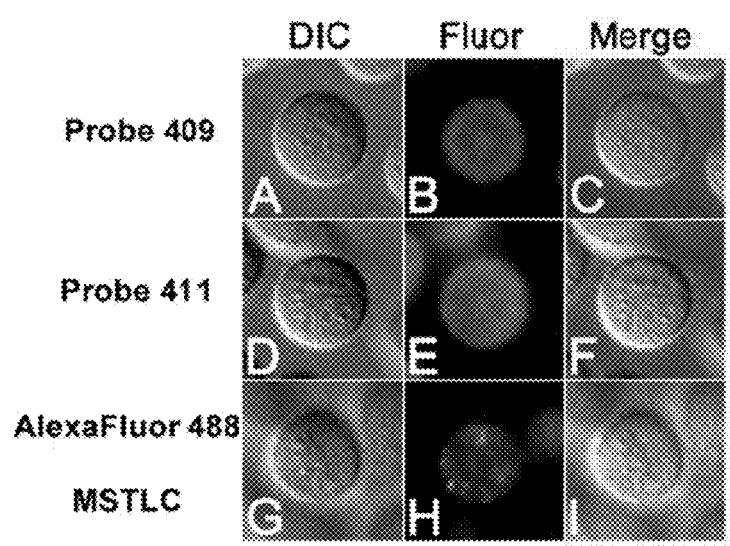
FIG. 15 illustrates MSTLC probes in mitotic HeLa cells.

The titration curve shown in FIG. 15 was used to calculate and effective dose (ED) 50 value of 17.2 nM for E2-HPY(530). The ED50 for E2 was calculated to be 0.11 nM in the same experiment (data not shown). These data indicate that E2-HPY(530) induces ER-mediated transcription.

FIG. 7 illustrates that E2-HPY(530) treatment induces ER-mediated transcription. Ten point titration curve analysis obtained from Invitrogen's SelectScreen® Profiling Service demonstrates that E2-HPY(530) has an ED50 value of 17.2 nM.

Figure 8:
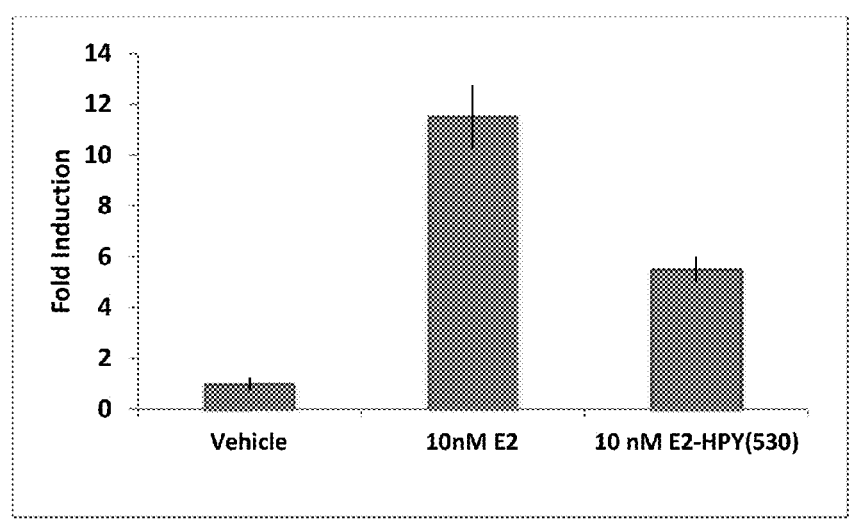
FIG. 8 is a graph illustrating how E2-HPY(530) treatment induces progesterone receptor (PR) gene transcription in MCF7 breast cancer cells.

FIG. 8 illustrates that E2-HPY(530) treatment induces the transcription of the estrogen receptor (ER)-responsive progesterone receptor gene in MCF7 breast cancer cells. Real-Time PCR analysis demonstrates that E2-HPY(530) induces the expression of the endogenous ER-responsive progesterone receptor gene in MCF7 cells (see FIG. 8) 2.0× $10^5$ MCF7 cells were seeded in 6 well plates and grown for 24 hours in DMEM containing 10% FBS. Prior to treatment, media was removed, cells were washed with PBS, grown in phenol red-free DMEM containing 10% charcoal-stripped FBS for about 24 hours. After 24 hours, cells were treated with 10 nM E2, 10 nM E2-HPY(530), or vehicle (ethanol) in phenol red-free DMEM containing 10% charcoal-stripped FBS for about 4 hours. Cells were trypsinized, collected and centrifuged at 1000 rpm for about 5 minutes. The supernatant was removed and the pellet stored at about −20° C. until RNA was isolated using RNEasy mini kit (Qiagen). cDNA synthesis was synthesized by reverse transcriptase PCR (Invitrogen) and real-time PCR analysis with SYBR green (Bio-Rad) was performed using PCR specific primers for human progesterone receptor.

FIG. 8 illustrates that E2-HPY(530) treatment induces progesterone receptor (PR) gene transcription in MCF7 breast cancer cells. Real-time PCR analysis of PR gene transcription in MCF7 cells treated for about 4 hours with 10 nM E2, 10 nM E2-HPY(530), or vehicle (ethanol) in phenol red-free DMEM containing 10% charcoal-stripped FBS. Data represent average fold induction of three independent experiments. Error bars represent the standard error of the mean (SEM).

Figure 9:
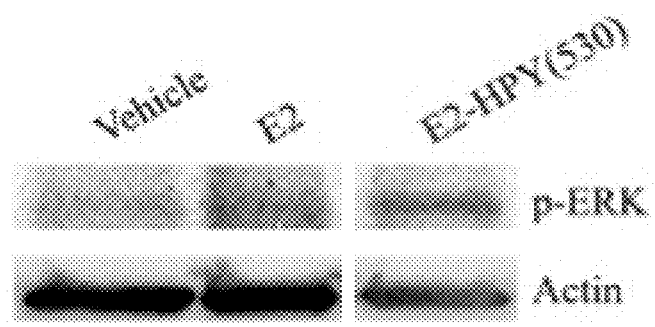
FIG. 9 shows that E2-HPY(530) treatment leads to the accumulation of phospho-ERK in MCF7 breast cancer cells.

FIG. 9 illustrates that E2-HPY(530) treatment leads to the accumulation of phospho-ERK in MCF7 breast cancer cells. The accumulation of phospho-ERK upon E2 treatment is a well-documented, non-genomic consequence of E2 treatment in MCF7 cells. To determine if E2-HPY(530) treatment also results in the accumulation of phospho-ERK in MCF7 cells, cells were treated with 10 nM E2, 10 nM E2-HPY(530), or vehicle (ethanol) in phenol red-free DMEM containing 10% charcoal-stripped FBS. After about a 15 minute treatment, protein lysates were isolated for immunoblot analysis. The upper panel of FIG. 17 was probed with pERK1/2 mAb (1:600, Santa Cruz Biotechnology) overnight at about 4° C. Lower panel was obtained after stripping the membrane and probing (1:3000) with Actin mAb overnight at about 4° C. Primary antibodies were visualized with horseradish peroxidase conjugated secondary antibodies.

FIG. 9 illustrates that E2-HPY(530) treatment leads to the accumulation of phospho-ERK in MCF7 breast cancer cells. About a 15 minute treatment of MCF7 cells with 10 nM E2 and 10 nM E2-HPY(530) resulted in the accumulation of phospho-ERK (p-ERK). Primary antibody raised against P-ERK was used to visualize p-ERK levels. Actin expression determined by Actin specific mAb was used as a loading control.

Figure 10:
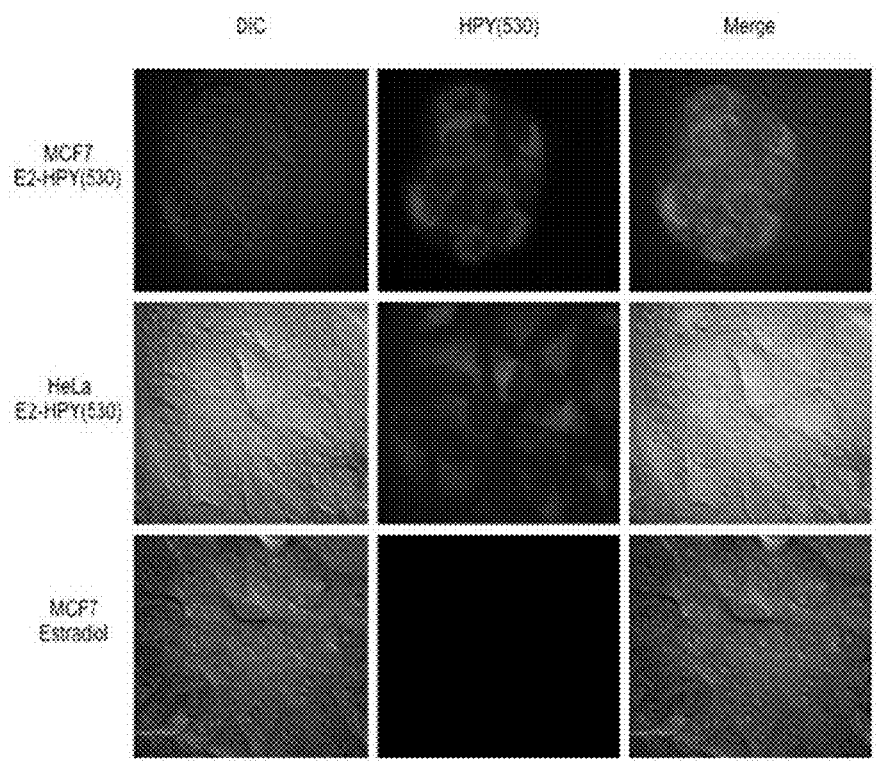
FIG. 10 illustrates that E2-HPY(530) accumulates throughout HeLa and MCF7 cells.
Figure 11:
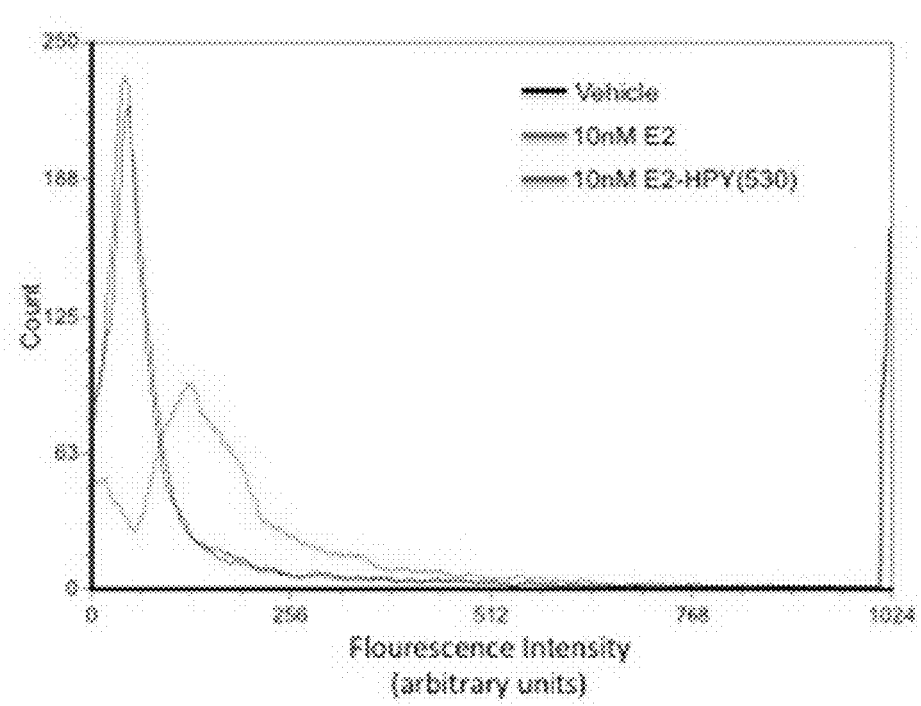
FIG. 11 illustrates that E2-HPY(530) is detectable in MCF7 cells by flow cytometry.

FIG. 10 and FIG. 11 illustrate that E2-HPY(530) accumulates in cells and can be detected by fluorescence microscopy and flow cytometry. MCF7 and HeLa cells were treated with 10 nM E2, 10 nM E2-HPY(530) and the presence of E2-HPY(530) was observed throughout the cells (FIG. 18). Cells were grown on 35 mm tissue culture dish with cover glass bottom (World Precision Instruments, Inc., FL). Following E2 or E2-HPY treatment for about six hours, the dish was transferred to a heated stage (about 37° C.) and DIC and/or fluorescence images of live cells were captured using 63×1.2 NA water objective mounted on an Axiovert 200M inverted microscope (Carl Zeiss, Thornwood, N.Y.) designed for standard wide-field epifluorescence. Images were acquired with a 12-bit AxioCam MrM charge-coupled device camera driven by Axiovision 4.5 software (Carl Zeiss). Equivalent exposures were acquired for each condition. The acquired images were then exported as 8 bit jpegs and figures were prepared using Photoshop version CS2 software (Adobe Systems, Mountain View, Calif.).

FIG. 10 illustrates that E2-HPY(530) accumulates throughout HeLa and MCF7 cells. Live cell imaging indicates that E2-HPY(530) is readily visible in both HeLa and MCF7 cells about six hours after treatment.

FIG. 11 illustrates that E2-HPY(530) is detectable in MCF7 cells by flow cytometry. MCF7 cells were treated for about six hours with 10 nM E2, 10 nM E2-HPY(530), or vehicle (ethanol) in phenol red-free DMEM containing about 10% charcoal-stripped FBS were then removed by trypsinization and centrifuged (250 g) for about five minutes. The supernatant was removed and the pellets were re-suspended in 1 mL of PBS and analyzed on the FACS Vantage (Becton Dickenson) retrofitted with a 300 mw 532 nm laser (Oxxius) and emission was detected using a 540 nm long pass filter.

FIG. 11 illustrates that E2-HPY(530) is detectable in MCF7 cells by flow cytometry. Increased fluorescence intensity is shown in arbitrary units and measured after excitation with a 532 nm laser and detection using a 540 nm long pass filter. 10,000 events were measured and the geometric mean for vehicle is 57.6, for E2 is 61.22, an for E2-HPY(530) is 124.2.

Fluorescence Polarization. The fluorescence characteristics E2-HPY(530) in aqueous suspension was characterized and validated for concentrations ranging from 250 nM to 2 mM. Additionally, a fluorescence polarization value of about 0.250 was determined for all concentrations tested. The ability to detect fluorescence emission and determine polarization values at relatively low concentrations of E2-HPY(530) is a unique property that can be used for biological experimentation such as ligand binding assays.

Computational studies were undertaken to understand the three dimensional structural features and the estrogenic-agonist activity of E2-HPY(530) using computer aided docking studies of this ligand in the hERα binding domain. All calculations were performed on a computer equipped with 1.6 GHz Core2 duo processor, 4 GB RAM and running with Windows 7. Ligand structures were built and energy minimized by using Spartan 10.0 (Wavefunctions, Inc, Irvine, Calif.). Docking studies were done by using GOLD 5.0.1 distributed by CCDC (Cambridge Crystallographic Data Center, Cambridge, UK). GOLD provides a docking tool for predicting the binding modes of small molecules into protein binding site. The crystal structure of PDB code: 2YAT which contains the hERα ligand-binding domain bound with an estradiol-europium complex (EPTA-Eu) was used for docking. This ligand also exhibits agonist behavior, like estradiol (E2) and E2-HPY(530), stimulating cell proliferation and inducing PR gene transcription in ERα-positive breast cancer cells. GOLD (Genetic Optimization for Ligand Docking) was used for the docking studies. The ligand EPTA-Eu was removed from the crystal structure and docked with E2-HPY(530) and estradiol (E2). 50 GA runs were carried out with standard default GOLD settings, a population size of 100, a maximum of 1,000,000 operations were performed. Scores were derived for 10 poses, and the highest score pose was selected for comparison. Ligand Scout v 3.0 was used for visual inspection of the docked poses in the ligand binding domain. The ERα-Ligand Binding Domain with E2-HPY(530) exhibits a three-layer helical "sandwich" fold and the probe occupies a buried, hydrophobic ligand-binding pocket (LBP), the steroid structure of E2-HPY(530) overlays closely with estradiol. The highest scoring poses of E2-HPY(530) and E2 gave GOLD scores 69.97 and 50.38. The overlay structure of E2-HPY-530 and E2 demonstrates that these compounds bind to the receptor in very similar orientation, which is consistent with the observed agonist activity.

Figures 12A, 12B, 12C:
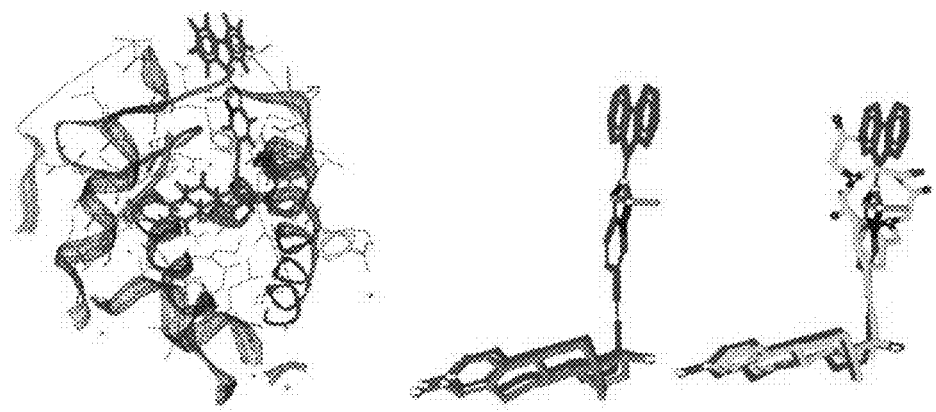
FIG. 12A-12C are cross-sectional 3D-bound views of the $E_2$-HPY-530 interactions with the ERα ligand binding domain.

FIGS. 12A-12C illustrated a cross-sectional 3D-bound view of the $E_2$-HPY-530 (red) interactions with the ERα ligand binding domain. The complex model of $E_2$-HPY-530/hERα was generated from structural coordinates downloaded from the Protein Data Bank (PDB ID: 2YAT). The complex model of E2-HPY(530)/hERα was generated from GOLD and highest scoring pose in LBD was shown in the central and right hand figures. Overlay pictures of $E_2$-HPY-530 with $E_2$ (blue) and $E_2$-HPY-530 with EPTA-Eu complex (green). The pictures were generated with Ligand Scout v 3.0 (Inteligand GmbH: Vienna, Austria, 2010).

Examples for HPY(405a)-Butynyl-MSTLC

HPY dyes can be used for labeling other molecular entities to produce fluorescent probes. A variety of chemistries can be used to result in the formation of covalent bonds for attaching the HPY dyes to other molecular entities. To exemplify this approach for the attachment of a HPY dye to a biologically active synthetic molecule, the following three conjugates of methoxy-5-trityl-L-cysteine (MSTLC) were synthesized:

HPY(405a)-Butynyl-MSTLC, designated (3.3): Structure I: $R_1$, $R_2$=methyl, $R_3$, $R_4$, $R_6$=H, $R_5$=[(2R)-2-amino-3-[[(4-methoxyphenyl)diphenylmethyl]thio]-N-[4-[3-butyn-1-yl] propanamide

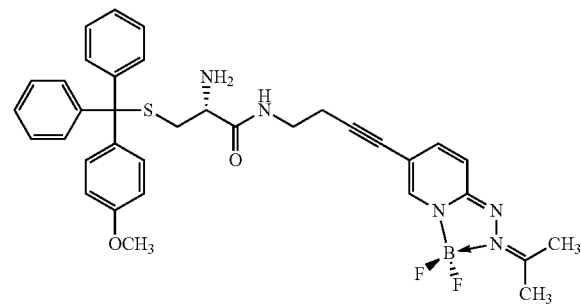

HPY(405a)-Butynyl-MSTLC
Chemical Formula: $C_{35}H_{36}BF_2N_5O_2S$
Molecular Weight: 639.57
3.3

Dimethoxy-HPY(405a)-Butynyl-MSTLC (3.5): Structure III: X=$OCH_3$, $R_1$, $R_2$=methyl, $R_3$, $R_4$, $R_6$=H, $R_5$=[(2R)-2-amino-3-[[(4-methoxyphenyl)diphenylmethyl]thio]-N-[4-[3-butyn-1-yl]propanamide

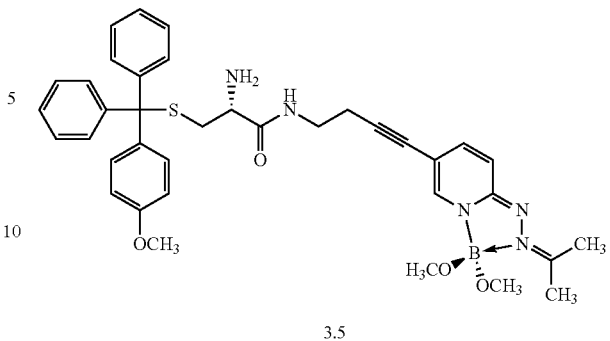

3.5

MSTLC-AlexaFluor® 488: contains a commercially available fluorescent dye for comparison.

Figure 13:
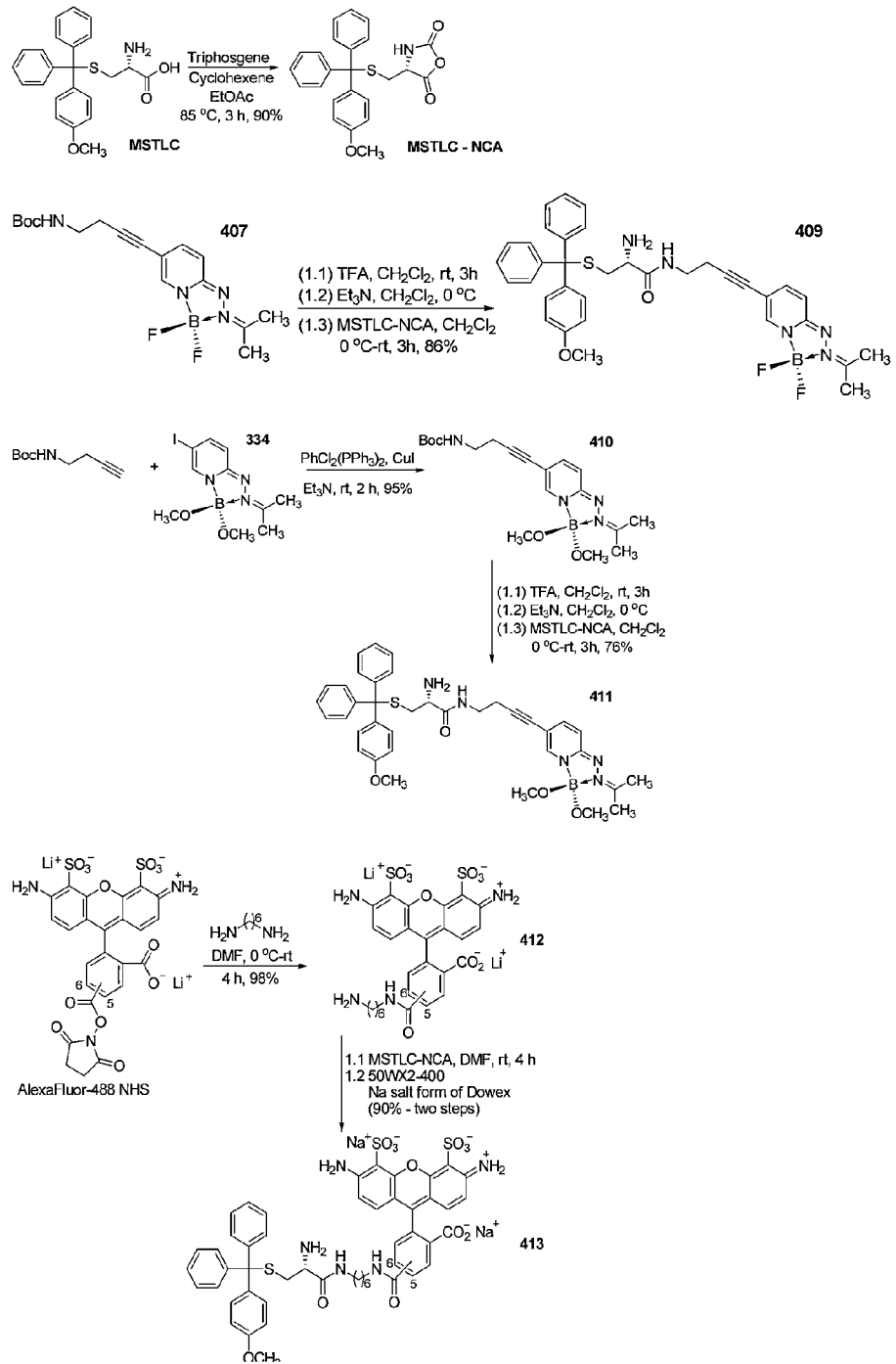
FIG. 13 illustrates an example synthesis of MSTLC-Probes.
Figure 14:
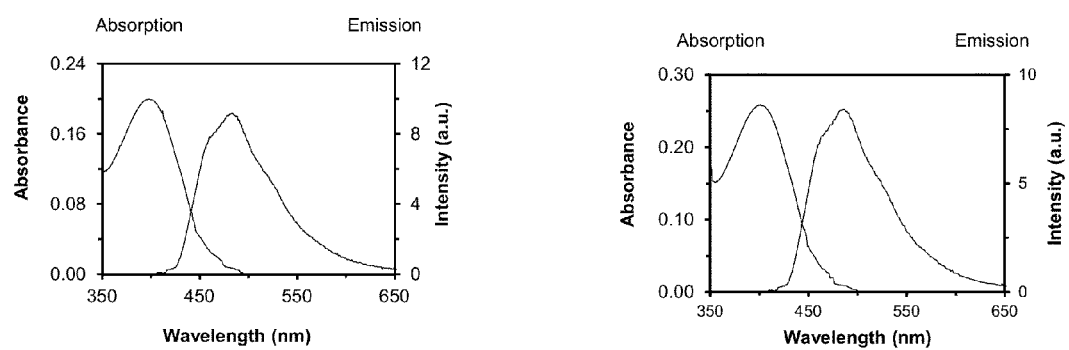
FIG. 14 illustrates UV-Vis absorption and emission spectra of MSTLC-HPY probes.

The synthetic steps used to synthesize the two HPY-probes (3.3 and 3.5) and the AlexaFluor®-probe (413) are shown in FIG. 13. These fluorescent probes were evaluated and compared in different assays. The photophysical properties (merged absorption and emission spectra) of the two MSTLC-HPY probes (3.3 and 3.5) are shown in FIG. 14. The photophysical properties of probes 3.3 and 3.5 were measured using 20 μM concentration in 1% DMSO/PBS at pH 7.4. The absorption maximum of 3.3=400 nm with a molar extinction coefficient=9900 $M^{-1}$ $cm^{-1}$. The probe 3.3 was excited at 400 nm and exhibited a fluorescence emission maximum=489 nm. The probe 3.5 showed an absorption maximum=400 nm, the molar extinction coefficient=12900 $M^{-1}$ $cm^{-1}$, and showed an emission maximum $\lambda_{em}$=486 nm when excited at 400 nm. Quantum yields of probes 3.3 and 3.5 were measured using coumarin 30 as the standard and found: 0.29 for 3.3 and 0.31 for 3.5. There were no substantial changes in the spectroscopic properties of the HPY-dyes due to the attachment of the MSTLC group.

The biological activity of the MSTLC-Probes was tested in mitotic HeLa cells and the results are shown in FIG. 15. FIG. 15 shows live imaging of mitotic HeLa cells treated with 3.3, 3.5 and MSTLC-AlexaFluor® 488 413. Treated cells formed monopolar spindles associated with RSP (Eg5) inhibition. The charged AlexaFluor probe exhibited punctate fluorescence (G-I).

FIG. 15 demonstrates that all three probes resulted in cells exhibiting the phenotypic monopolar spindle structure associated with inhibition of human kinesin Eg5. These results demonstrate that the conjugation of the dyes to the MSTLC compound produces probes with the same type of biological activity. The mitotic cells treated with MSTLC-HPY probes 3.3 and 3.5 display diffuse fluorescence throughout the cytoplasm, consistent with the expectations for cell membrane permeability of these HPY-compounds. The fluorescence in cells treated with MSTLC-AlexaFluor® 488 413 was different, confined to punctate structures, presumably within the acidic endosome compartments.

Figure 16:
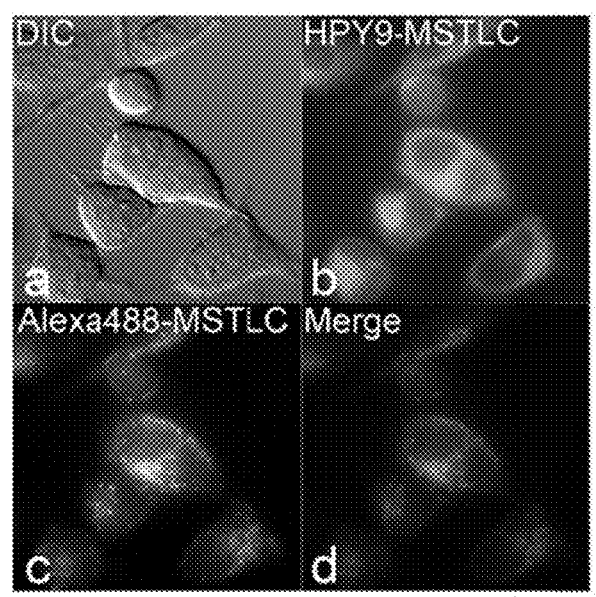
FIG. 16 illustrates live cell imaging of HeLa cells in interphase treated with dimethoxy-HPY(405a)-Butynyl-MSTLC and MSTLC-AlexaFluor 488.

Fluorescence images of interphase HeLa cells treated with MSTLC-Probes is shown in FIG. 16. FIG. 16 shows live cell imaging of HeLa cells in interphase simultaneously treated with 3.5 and MSTLC-AlexaFluor® 488 413, (a) DIC; (b) 3.5 fluorescent image; (c) 413 fluorescent image in black and white; and (d) Merged fluorescent image. These cells appear normal because the KSP (Eg5) motor protein is only required during mitosis, therefore the MSTLC-Probes do not have an observable biological effect. The fluorescence shows a difference between the neutral HPY probes and charged Alexa Fluor probe 413. These images clearly show that the probe 3.5 diffuses into the cell and is distributed evenly inside the cytoplasm. The charged Alexa Fluor probe 413 produced punctuated images that are consistent with uptake by endocytosis and localization in intracellular vesicles that are not available to diffuse into the cytoplasm.

Figure 17:
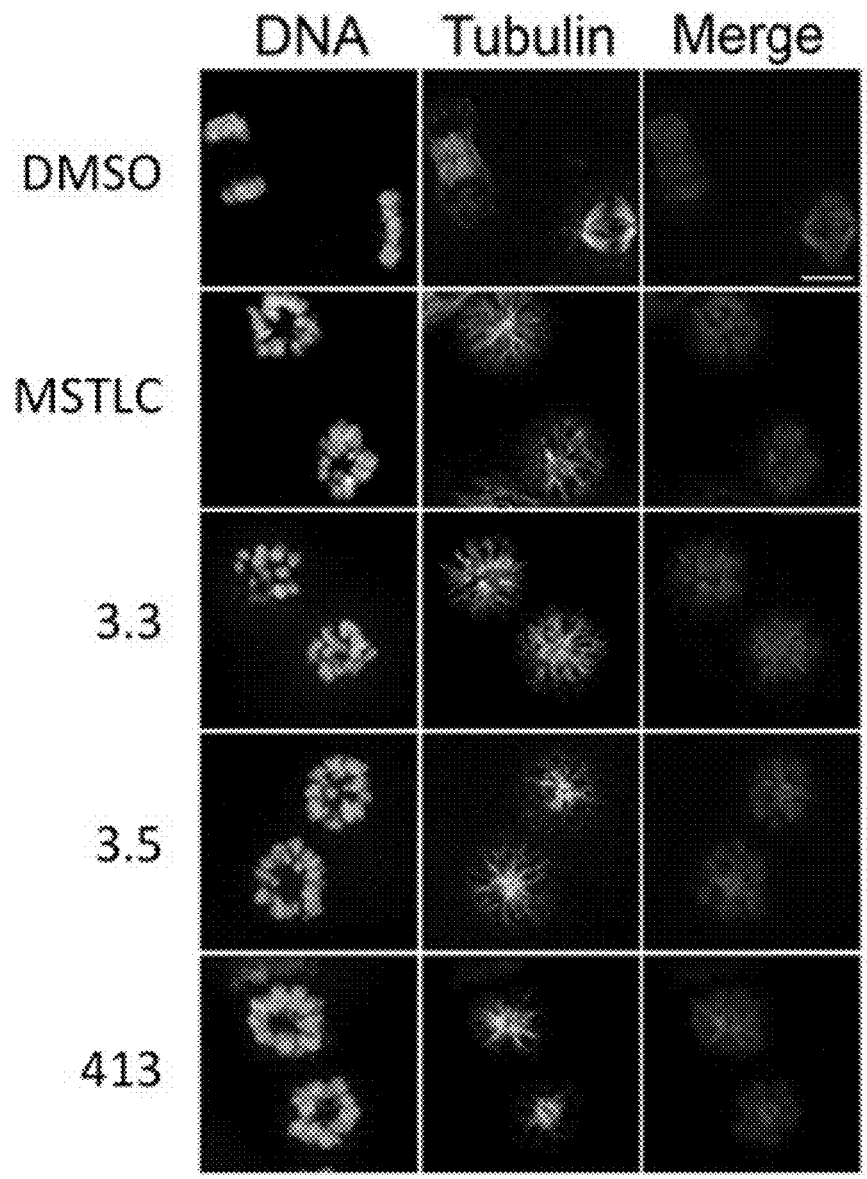
FIG. 17 illustrates a comparison of monopolar spindles from treatment with MSTLC-probes.

The inhibitory activity of human kinesin Eg5 motor protein was tested using probes 3.3, 3.5 and 413. HeLa cells were treated with 10 μM of each probe, as well as the unconjugated inhibitor Methoxy-S-Trityl-L-cysteine. Then cells were incubated with anti-α tubulin 1:1000 primary antibody, AlexaFluor-546 conjugated rabbit anti-mouse secondary antibody and Hoechst 33342 for staining microtubules and DNA respectively. Cells were subsequently washed and mounted onto glass sides with 90% glycerol and imaged using a Zeiss Axiovert 200M inverted microscope outfitted with epifluorescence optics, and a Zeiss Apotome structured illumination module. FIG. 17 shows tubulin and DNA location in HeLa cells treated with carrier control (0.1% DMSO), MSTLC, probes 3.3, 3.5 and MSTLC-AlexaFluor® 488 413. While all MSTLC-dye conjugates were effective in generating monopolar spindles, the MSTLC-HPY Probes 3.3 and 3.5 produced greater amounts of monopolar spindles associated with inhibition of the KSP (Eg5) motor protein, with calculated effective concentration (EC50) values of about 1.13 and 1.03 μM respectively. In contrast, the charged Alexa Fluor probe 413 blocked bipolar spindle with an EC50 of about 5.4 μM. These results demonstrate the MSTLC-HPY Probes were effective inhibitors of KSP Eg5 in cells, and the relatively small, neutral HPY dye structure conferred advantages over a large charged dye (Alexa Fluor 488) when used for an intracellular target that is located in the cytoplasm.

The preceding example as well as the following example can be repeated with similar success by substituting the generically or specifically described reactants and/or operating conditions of this invention for those used in the preceding examples. Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A fluorescent composition having Formula I, or its enantiomer, diastereomer, stereoisomer, and pharmaceutical salt thereof, wherein Formula I is:

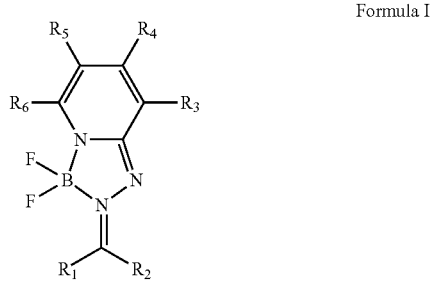

Formula I wherein, $R_1$ and $R_2$ are independently selected from H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic compound, heterocyclic compound, heterocyclic aromatic compound, aromatic compound;

$R_3$, $R_4$, $R_5$, and $R_6$ are independently selected from H, F, Cl, Br, I, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, thiol, sulfide, sulfoxide, sulfone, sulfonate, sulfoximine, urea, carbamate, maleimide, triazole, tetrazine, isothiocyanate, thiourea, linear or branched carbon chain or ring, the carbon chain or ring optionally substituted with F, Cl, Br, I or a $C_1$ to $C_{27}$ carbon substituted compound, acyl, heterocyclic compound, heterocyclic aromatic compound, aromatic compound, enol, enolate, ester enolate, amide;

wherein $R_1$ is not phenyl or 4-(thiophen-2-yl)phenyl;

wherein $R_2$ is not phenyl or 4-(thiophen-2-yl)phenyl; and wherein $R_5$ is not Br or 4-phenyl-1H-1,2,3-triazol-1-yl.

2. The fluorescent composition of claim 1 wherein $R_5$ of Formula I is attached to a molecule to produce a conjugated entity.

3. The fluorescent composition of claim 2 wherein the molecule is selected from a carbohydrate, a lipid, triacylglycerol, sterol, fatty acid ester, phospholipid, phosphoglyceride, sphingolipid, ceramide, an amino acid, a peptide, a protein, antibody, a nucleic acid, a steroid, a vitamin, a cofactor, or a biotin.

4. The fluorescent composition of claim 2 wherein the molecule is selected from a biologically active compound, an enzyme inhibitor, an agonist, an antagonist, anticancer, antimicrobial, antiviral, antifungal, antiparasitic, antiinflammatory, cardiovascular, antidiabetic, a pharmaceutical, and analogs thereof.

5. The fluorescent composition of claim 2 wherein the molecule comprises a 17-alpha-ethynylestradiol.

6. The fluorescent composition of claim 1 wherein $R_1$ and $R_2$ of Formula I together form a cyclopentyl.

7. The fluorescent composition of claim 6 wherein $R_5$ of Formula I is a carboxy-succinimidyl ester, $R_3$ of Formula I is a H, $R_4$ of Formula I is a H, and $R_6$ of Formula I is a H.

8. The fluorescent composition of claim 6 wherein $R_5$ of Formula I is a but-3-yn-1-amine, $R_3$ of Formula I is a H, $R_4$ of Formula I is a H, and $R_6$ of Formula I is a H.

9. The fluorescent composition of claim 6 wherein $R_5$ of Formula I is a but-4-yl-1-amine, $R_3$ of Formula I is a H, $R_4$ of Formula I is a H, and $R_6$ of Formula I is a H.

10. The fluorescent composition of claim 6 wherein $R_5$ of Formula I is a 4-butyl-1-triphenylphosphonium-3-propanamide, $R_3$ of Formula I is a H, $R_4$ of Formula I is a H, and $R_6$ of Formula I is a H.

11. The fluorescent composition of claim 6 wherein $R_5$ of Formula I is a N-(2-(2-(2-(2-azidoethoxy)ethoxy)ethoxy)ethyl)carboxamide, $R_3$ of Formula I is a H, $R_4$ of Formula I is a H, and $R_6$ of Formula I is a H.

12. The fluorescent composition of claim 1 wherein $R_1$ and $R_2$ of Formula I together form a substituted fluorene

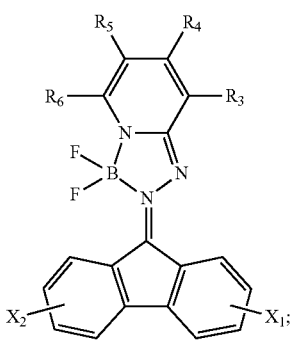

wherein X₁ and X₂ are independently selected from H, linear or branched carbon chain or ring, optionally substituted with F, Cl, Br, I, $C_1$ to $C_{27}$ carbon substituted compound, alcohol, thiol, phenol, ether, epoxide, aldehyde, ketone, carboxylic acid, acyl halide, acid anhydride, ester, amide, alkyne, alkene, alkyl halide, aryl halide, amine, azide, nitrile, nitro compound, sulfide, sulfoxide, sulfone, sulfonate, sulfoximine, urea, carbamate, maleimide, triazole, tetrazine, isothiocyanate, thiourea, carbocyclic, compound, heterocyclic compound, heterocyclic aromatic compound, aromatic compound.

13. The fluorescent composition of claim 12 wherein X₁ is a H, X₂ is a H, R₅ of Formula I is a prop-2-enoic-tert-butyl ester, R₃ of Formula I is a H, R₄ of Formula I is a H, and R₆ of Formula I is a H.

14. The fluorescent composition of claim 12 wherein X₁ is a H, X₂ is a H, R₅ of Formula I is a N-(2-(2-(2-aminoethoxy) ethoxy)ethyl)carboxamide, R₃ of Formula I is a H, R₄ of Formula I is a H, and R₆ of Formula I is a H.

15. The fluorescent composition of claim 12 wherein X₁ is a H, X₂ is a H, R₅ of Formula I is a but-3-yn-1-amine, R₃ of Formula I is a H, R₄ of Formula I is a H, and R₆ of Formula I is a H.

16. The fluorescent composition of claim 12 wherein X₁ is a H, X₂ is a H, R₅ of Formula I is a but-4-yl-1-amine, R₃ of Formula I is a H, R₄ of Formula I is a H, and R₆ of Formula I is a H.

17. The fluorescent composition of claim 12 wherein X₁ is a H, X₂ is a H, R₅ of Formula I is a N-(2-(2-(2-(triphenylphosphonium-3-propanamido)ethoxy)ethoxy)ethyl)carboxamide, R₃ of Formula I is a H, R₄ of Formula I is a H, and R₆ of Formula I is a H.

18. The fluorescent composition of claim 12 wherein X₁ is a H, X₂ is a H, R₅ of Formula I is a but-3-yn-1-triphenylphosphonium-3-propanamide, R₃ of Formula I is a H, R₄ of Formula I is a H, and R₆ of Formula I is a H.

19. The fluorescent composition of claim 12 wherein X₁ is a H, X₂ is a H, R₅ of Formula I is a 4-butyl-1-triphenylphosphonium-3-propanamide, R₃ of Formula I is a H, R₄ of Formula I is a H, and R₆ of Formula I is a H.

20. The fluorescent composition of claim 12 wherein X₁ is a H, X₂ is a H, R₅ of Formula I is a carboxy-succinimidyl ester, R₃ of Formula I is a H, R₄ of Formula I is a H, and R₆ of Formula I is a H.

* * * * *